US007122328B2

(12) United States Patent
Kingsley et al.

(10) Patent No.: US 7,122,328 B2
(45) Date of Patent: Oct. 17, 2006

(54) GENE INVOLVED IN MINERAL DEPOSITION AND USES THEREOF

(75) Inventors: David Mark Kingsley, Stanford, CA (US); Michelle Deanetta Johnson, Tubingen (DE); Andrew Manlap Ho, Lexington, MA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 305 days.

(21) Appl. No.: 10/169,596

(22) PCT Filed: Jan. 5, 2001

(86) PCT No.: PCT/US01/00503

§ 371 (c)(1),
(2), (4) Date: Dec. 2, 2002

(87) PCT Pub. No.: WO01/49707

PCT Pub. Date: Jul. 12, 2001

(65) Prior Publication Data

US 2004/0242468 A1    Dec. 2, 2004

Related U.S. Application Data

(60) Provisional application No. 60/174,640, filed on Jan. 5, 2000.

(51) Int. Cl.
G01N 33/84 (2006.01)
G01N 33/53 (2006.01)
A61K 38/16 (2006.01)

(52) U.S. Cl. .................. 435/7.21; 435/7.92; 530/350; 530/352

(58) Field of Classification Search ............... 530/350, 530/352; 435/69.2
See application file for complete search history.

(56) References Cited

FOREIGN PATENT DOCUMENTS

WO      WO 99/046281        *    9/1999

OTHER PUBLICATIONS

Numberg et al, Nature Genetics 28: 37-41, May 2001.*
Ngo et al., 1994, The Protein Folding Problem and Tertiary Structure Prediction, pp. 491-495.*
Stryer et al, in Biochemistry, Third edition, W H Freeman Company, New York, pp. 31-33, 1998.*
Andrew et al., (1999), *Am. J. Hum. Genet.*, 64:136-45.
Badley et al., (1994), *J. Rheumatol.*, 21:505-14)
Baldwin et al., (1995), *Am. J. Hum. Genet.*, 56:692-7.
Fam, A.G., (1995), *Curr. Opin. Rheumatol.*, 7:364-8.
Felson et al., (1989), *J. Rheumatol.*, 16:1241-5.
Gerster, J.C., (1994), *J. Rheumatol.*, 21:2164-5.
Hakim et al., (1984), *Arthritis Rheum.*, 27:1411-20.
Hakim, et al., (1986), *Arthritis Rheum.*, 29(1), 114-123.
Hughes et al., (1995), *Hum. Mol. Genet.*, 4:1225-8.
Huskisson et al., (1979), *Ann. Rheum. Dis.*, 38:423-8.
Ledingham et al., (1993), *Ann. Rheum. Dis.*, 52:520-6.
Mahowald et al., (1989), *J. Rheumatol.*, 16:60-6.
Sampson et al., (1991), *Acta Anat. (Basel)*, 141:36-41.
Sampson, H.W., (1988), *Am. J. Anat.*, 182:257-69.
Sampson, H.W., (1988), *Spine*, 13:645-9.
Sweet and Green, (1981), *J. Hered.*, 72:87-93.

\* cited by examiner

*Primary Examiner*—Christina Chan
*Assistant Examiner*—Phuong Huynh
(74) *Attorney, Agent, or Firm*—Pamela J. Sherwood; Bozicevic, Field & Francis LLP

(57) ABSTRACT

The present invention features a novel human protein (ANK), nucleotide sequences encoding human ANK, and assays for ANK activity, including assays to identify therapeutics and diagnostic assays, e.g., for susceptibility to diseases such as arthritis. In related aspects the invention features expression vectors and host cells comprising polynucleotides that encode a human ANK. The present invention also relates to antibodies that bind specifically to a human ANK, and methods for producing human ANK polypeptides.

6 Claims, No Drawings

SEQUENCE LISTING

```
<160> NUMBER OF SEQ ID NOS: 114

<210> SEQ ID NO 1
<211> LENGTH: 1570
<212> TYPE: DNA
<213> ORGANISM: Homo sapiens
<220> FEATURE:
<221> NAME/KEY: misc_feature
<222> LOCATION: (1)...(1570)
<223> OTHER INFORMATION: n = A,T,C or G

<400> SEQUENCE: 1
nnttactcag ctccccgcag agtcccctcg cggcagcaga tgtgtgtggg gtcagcccac      60
ggcggggact atggtgaaat tcccggcgct cacgcactac tggcccctga tccggttctt     120
ggtgcccctg ggcatcacca acatagccat cgacttcggg gagcaggcct tgaaccgggg     180
cattgctgct gtcaaggagg atgcagtcga gatgctggcc agctacgggc tggcgtactc     240
cctcatgaag ttcttcacgg gtcccatgag tgacttcaaa aatgtgggcc tggtgtttgt     300
gagcagcaag agagacagga ccaaagccgt cctgtgtatg gtggtggcag gggccatcgc     360
tgctgtcttt cacacnctga tagcttatag tgatttagga tactacatta tcaataaact     420
gcaccatgtg gacgagtcgg tggggagcaa gacgagaagg gccttcctgt acctcgccgc     480
ctttcctttc atggacgcaa tggcatggac ccatgctggc attctcttaa aacacaaata     540
```

-continued

```
cagtttcctg gtgggatgtg cctcaatctc agatgtcata gctcaggttg tttttgtagc      600
cattttgctt cacagtcacc tggaatgccg ggagccctg ctcatcccga tcctctcctt       660
gtacatgggc gcacttgtgc gctgcaccac cctgtgcctg gctactaca agaacattca       720
cgacatcatc cctgacagaa gtggcccgga gctgggggga gatgcaacaa taagaaagat     780
gctgagcttc tggtggcctt tggctctaat tctggccaca cagagaatca gtcggcctat      840
tgtcaacctc tttgtttccc gggaccttgg tggcagttct gcagccacag aagcagtggc     900
gattttgaca gccacatacc ctgtgggtca catgccatac ggctggttga cggaaatccg      960
tgctgtgtat cctgctttcg acaagaataa ccccagcaac aaactggtga gcacgagcaa     1020
cacagtcacg gcagcccaca tcaagaagtt caccttcgtc tgcatggctc tgtcactcac     1080
gctctgttc gtgatgtttt ggacacccaa cgtgtctgag aaaatcttga tagacatcat     1140
cggagtggac tttgcctttg cagaactctg tgttgttcct ttgcggatct tctccttctt     1200
cccagttcca gtcacagtga gggcgcatct caccgggtgg ctgatgacac tgaagaaaac     1260
cttcgtcctt gccccagct ctgtgctgcg gatcatcgtc ctcatcgcca gcctcgtggt     1320
cctaccctac ctgggggtgc acggtgcgac cctgggcgtg ggctccctcc tggcgggctt     1380
tgtgggagaa tccaccatgg tcgccatcgc tgcgtgctat gtctaccgga agcagaaaaa     1440
gaagatggag aatgagtcgg ccacggaggg ggaagactct gccatgacag acatgcctcc     1500
gacagaggag gtgacagaca tcgtggaaat gagagaggag aatgaataag cagcccacg     1560
gccatgggca                                                            1570
```

<210> SEQ ID NO 2
<211> LENGTH: 492
<212> TYPE: PRT
<213> ORGANISM: Homo sapiens

<400> SEQUENCE: 2

```
Met Val Lys Phe Pro Ala Leu Thr His Tyr Trp Pro Leu Ile Arg Phe
  1               5                  10                  15

Leu Val Pro Leu Gly Ile Thr Asn Ile Ala Ile Asp Phe Gly Glu Gln
             20                  25                  30

Ala Leu Asn Arg Gly Ile Ala Ala Val Lys Glu Asp Ala Val Glu Met
         35                  40                  45

Leu Ala Ser Tyr Gly Leu Ala Tyr Ser Leu Met Lys Phe Phe Thr Gly
     50                  55                  60

Pro Met Ser Asp Phe Lys Asn Val Gly Leu Val Phe Val Ser Ser Lys
 65                  70                  75                  80

Arg Asp Arg Thr Lys Ala Val Leu Cys Met Val Ala Gly Ala Ile
                 85                  90                  95

Ala Ala Val Phe His Thr Leu Ile Ala Tyr Ser Asp Leu Gly Tyr Tyr
            100                 105                 110

Ile Ile Asn Lys Leu His His Val Asp Glu Ser Val Gly Ser Lys Thr
        115                 120                 125

Arg Arg Ala Phe Leu Tyr Leu Ala Ala Phe Pro Phe Met Asp Ala Met
    130                 135                 140

Ala Trp Thr His Ala Gly Ile Leu Leu Lys His Lys Tyr Ser Phe Leu
145                 150                 155                 160

Val Gly Cys Ala Ser Ile Ser Asp Val Ile Ala Gln Val Val Phe Val
                165                 170                 175

Ala Ile Leu Leu His Ser His Leu Glu Cys Arg Glu Pro Leu Leu Ile
```

-continued

```
                  180                 185                 190
Pro Ile Leu Ser Leu Tyr Met Gly Ala Leu Val Arg Cys Thr Thr Leu
            195                 200                 205

Cys Leu Gly Tyr Tyr Lys Asn Ile His Asp Ile Ile Pro Asp Arg Ser
        210                 215                 220

Gly Pro Glu Leu Gly Gly Asp Ala Thr Ile Arg Lys Met Leu Ser Phe
225                 230                 235                 240

Trp Trp Pro Leu Ala Leu Ile Leu Ala Thr Gln Arg Ile Ser Arg Pro
                245                 250                 255

Ile Val Asn Leu Phe Val Ser Arg Asp Leu Gly Gly Ser Ser Ala Ala
            260                 265                 270

Thr Glu Ala Val Ala Ile Leu Thr Ala Thr Tyr Pro Val Gly His Met
        275                 280                 285

Pro Tyr Gly Trp Leu Thr Glu Ile Arg Ala Val Tyr Pro Ala Phe Asp
290                 295                 300

Lys Asn Asn Pro Ser Asn Lys Leu Val Ser Thr Ser Asn Thr Val Thr
305                 310                 315                 320

Ala Ala His Ile Lys Lys Phe Thr Phe Val Cys Met Ala Leu Ser Leu
                325                 330                 335

Thr Leu Cys Phe Val Met Phe Trp Thr Pro Asn Val Ser Glu Lys Ile
            340                 345                 350

Leu Ile Asp Ile Ile Gly Val Asp Phe Ala Phe Ala Glu Leu Cys Val
        355                 360                 365

Val Pro Leu Arg Ile Phe Ser Phe Phe Pro Val Pro Val Thr Val Arg
370                 375                 380

Ala His Leu Thr Gly Trp Leu Met Thr Leu Lys Lys Thr Phe Val Leu
385                 390                 395                 400

Ala Pro Ser Ser Val Leu Arg Ile Ile Val Leu Ile Ala Ser Leu Val
                405                 410                 415

Val Leu Pro Tyr Leu Gly Val His Gly Ala Thr Leu Gly Val Gly Ser
            420                 425                 430

Leu Leu Ala Gly Phe Val Gly Glu Ser Thr Met Val Ala Ile Ala Ala
        435                 440                 445

Cys Tyr Val Tyr Arg Lys Gln Lys Lys Lys Met Glu Asn Glu Ser Ala
450                 455                 460

Thr Glu Gly Glu Asp Ser Ala Met Thr Asp Met Pro Pro Thr Glu Glu
465                 470                 475                 480

Val Thr Asp Ile Val Glu Met Arg Glu Glu Asn Glu
                485                 490

<210> SEQ ID NO 3
<211> LENGTH: 170
<212> TYPE: DNA
<213> ORGANISM: Homo sapiens
<220> FEATURE:
<221> NAME/KEY: misc_feature
<222> LOCATION: (1)...(170)
<223> OTHER INFORMATION: n = A,T,C or G

<400> SEQUENCE: 3
nnnttactca gctccccgca gagtcccctc gcggcagcag atgtgtgtgg ggtcagccca      60
gcccggggac tatggtgaaa ttcccggcgc tcacgcacta ctggcccctg atccggttct     120
tggtgcccct gggcatcacc aacatagcca tcgacttcgg ggagcagnnn                170

<210> SEQ ID NO 4
```

<211> LENGTH: 416
<212> TYPE: DNA
<213> ORGANISM: Homo sapiens
<220> FEATURE:
<221> NAME/KEY: misc_feature
<222> LOCATION: (1)...(416)
<223> OTHER INFORMATION: n = A,T,C or G

<400> SEQUENCE: 4

```
tctatagaaa cgtgatctgc tgaatttcat cttagaggta tgattcccca gagaagagat      60
gacatttcta atgcttgtgg gttttttttcc cccttcccag gccttgaacc ggggcattgc    120
tgctgtcaag gaggatgcag tcgagatgct ggccagctac gggctggcgt actccctcat    180
gaagttcttc acgggtccca tgagtgactt caaaaatgtg gcctggtgt ttgtgagcag      240
caagagagac aggaccaaag ccgtcctgtg tatggtggtg gcaggggcca tcgctgctgt    300
ctttcacacn ctgataggtg aggccgccga ccgccactga cgaatctagc tttggcaatt    360
tcttattcct tttcattgat ttaaggagag gacagcgatt ctcgtacgaa cggtta        416
```

<210> SEQ ID NO 5
<211> LENGTH: 320
<212> TYPE: DNA
<213> ORGANISM: Homo sapiens

<400> SEQUENCE: 5

```
aaatactaca tttaaaattg ttttttaagct tttgaaacaa aagaatata aagatatcct      60
tttctaaata ttttccacata tgcctttcga ccactttgca gcttatagtg atttaggata   120
ctacattatc ataaaactgc accatgtgga cgagtcggtg gggagcaaga cgagaagggc    180
cttcctgtac ctcgccgcct ttcctttcat ggacgcaatg gtgagtagag aagatcgttg    240
gctttctttc ttttttcttta actggtggta aaatatacat aatataaaat ctaccatttt   300
agctattttt gtgtgtacag                                                320
```

<210> SEQ ID NO 6
<211> LENGTH: 284
<212> TYPE: DNA
<213> ORGANISM: Homo sapiens

<400> SEQUENCE: 6

```
ggtataaagt gtatttcagg aatgcccagt aaatctcaac aaccagaaac agcataatcc      60
tgaaggtgta tctcatgcca aattctttc tttctggcag gcatggaccc atgctggcat    120
tctcttaaaa cacaaataca gtttcctggt gggatgtgcc tcaatctcag atgtcatagc    180
tcaggtaaat atggtctgtg tgtcaatcag agctcctcag agtcccctc tggcgtgtgt     240
aactgatgtg tgatttatat tcattcactg tgcagtacac tctg                    284
```

<210> SEQ ID NO 7
<211> LENGTH: 371
<212> TYPE: DNA
<213> ORGANISM: Homo sapiens
<220> FEATURE:
<221> NAME/KEY: misc_feature
<222> LOCATION: (1)...(371)
<223> OTHER INFORMATION: n = A,T,C or G

<400> SEQUENCE: 7

```
gctcagaggt ntgtntcagg ttcaagagcg tgccctgtg nttctgtcag tcggttcccg       60
nttctcccct ctgacctgtt cccgttctcc cttctctcag gttgttttg tagccatttt     120
gcttcacagt cacctggaat gccgggagcc cctgctcatc ccgatcctct ccttgtacat    180
```

```
gggcgcactt gtgcgctgca ccaccctgtg cctgggctac tacaagaaca ttcacgacat    240
catccctgac agaagtggcc cggagctggg ggtacgtcta ccaacccaac agcagtctgt    300
ctgagactca gagtagaata aaactgtatt ccacctctat gtaaaatgag aaatcagtga    360
catcaaaaca t                                                         371
```

<210> SEQ ID NO 8
<211> LENGTH: 590
<212> TYPE: DNA
<213> ORGANISM: Homo sapiens
<220> FEATURE:
<221> NAME/KEY: misc_feature
<222> LOCATION: (1)...(590)
<223> OTHER INFORMATION: n = A,T,C or G

<400> SEQUENCE: 8

```
gcttccagcc agtccatttg atgagataac aaagacttta atttcaaacc tgtttctcag     60
ttggttagag attccccgag tctcagtatg gaaaagagtg gttgggatcc attaaacttc    120
agtgtgtgtt ttaatttcac agcagcttgc cagctgtctc ggttaatttc tattaggact    180
gaacatttta ttttaattca acttggcttg tctacagaca cttttcctta tattactttc    240
aagtatagtg aattggcttg tgattaacat acgaaggaaa agctttgatt ctgaatcgtt    300
ttttccattc tgcttctaga gttcaggtaa cttttatctt cgtttcttaa cacagggaga    360
tgcaacaata agaaagatgc tgagcttctg gtggcctttg gctctaattc tggccacaca    420
gagaatcagt cggcctattg tcaacctctt tgtttcccgg gaccttggtg gcagttctgc    480
agccacagaa gtgggccatg ctttgggat gtggggctta tgatcacctt ggtggggcaa     540
gggggtgctg aaactgattt cagttcttct cnagagctca agtaattccc                590
```

<210> SEQ ID NO 9
<211> LENGTH: 293
<212> TYPE: DNA
<213> ORGANISM: Homo sapiens

<400> SEQUENCE: 9

```
cagtggctgc acctgagtcg gcgtgcttcg tcacctactg tagctcctgg aggacttcct     60
gctggtaccc tgctaactct gccacctctt cctgttgcag gcagtggcga ttttgacagc    120 cacatacct gtgggtcaca tgccatacgg ctggttgacg gaaatccgtg ctgtgtatcc    180
tgctttcgac aaggtgagaa cccgtgcggt gtcgtgtctg aaacatgctt ttgaaatgac    240
ttcttgatag acagggctct ctgatgaggg acactttgtt gcttctcagt cct            293
```

<210> SEQ ID NO 10
<211> LENGTH: 296
<212> TYPE: DNA
<213> ORGANISM: Homo sapiens
<220> FEATURE:
<221> NAME/KEY: misc_feature
<222> LOCATION: (1)...(296)
<223> OTHER INFORMATION: n = A,T,C or G

<400> SEQUENCE: 10

```
acatcagata aancaaaagc aagatgntct tcaagatccc ccggtgggtt cagccaagga     60
taagccgggc ccattcatga ctgtggtttt ctttccccag aataacccca gcaacaaact    120
ggtgagcacg agcaacacag tcacggcagc ccacatcaag aagttcacct tcgtctgcat    180
ggctctgtca ctcacggtaa ggacagaggc tctctctgcc tcttctctct gtttggtttt    240
```

| tgtaaagggg caagttgcta tttttaaaggg ggaaatctta tttttccacaa tgtaat | 296 |

<210> SEQ ID NO 11
<211> LENGTH: 329
<212> TYPE: DNA
<213> ORGANISM: Homo sapiens
<220> FEATURE:
<221> NAME/KEY: misc_feature
<222> LOCATION: (1)...(329)
<223> OTHER INFORMATION: n = A,T,C or G

<400> SEQUENCE: 11

| cctctttcgt aactctccaa ggattgtgcc acacctgatc tgctcatttc acctgcttac | 60 |
| actttttcct cacaaccctg tttgatgtct ttctccccag ctctgtttcg tgatgttttg | 120 |
| gacacccaac gtgtctgaga aaatcttgat agacatcatc ggagtggact ttgccttttgc | 180 |
| agaactctgt gttgttcctt tgcggatctt ctccttcttc ccagttccag gtaaagaaaa | 240 |
| ncagaatgaa ggaagcattc ctgnttatcc tcatgcctaa ttaaatctttt ctttggaaat | 300 |
| gnttgcaatt atgtcaccna cacaaatgt | 329 |

<210> SEQ ID NO 12
<211> LENGTH: 326
<212> TYPE: DNA
<213> ORGANISM: Homo sapiens
<220> FEATURE:
<221> NAME/KEY: misc_feature
<222> LOCATION: (1)...(326)
<223> OTHER INFORMATION: n = A,T,C or G

<400> SEQUENCE: 12

| tagccagccc ttggntntng natgtgctgc ctngtccaga ggcagcagga tggggagtgt | 60 |
| atggcgggca cggctgacga gtcctttgtt cctcccaaca gtcacagtga gggcgcatct | 120 |
| caccgggtgg ctgatgacac tgaagaaaac cttcgtcctt gccccagct ctgtgctgcg | 180 |
| gatcatcgtc ctcatcgcca gcctcgtggt cctaccctac ctggggtatg ttgtcaggga | 240 |
| gtttggggct gtgggtcctt ctgccacttc aatactgtgt ccagaggttt aacagctaca | 300 |
| ttttcagggg aaatccccag gcacgt | 326 |

<210> SEQ ID NO 13
<211> LENGTH: 294
<212> TYPE: DNA
<213> ORGANISM: Homo sapiens

<400> SEQUENCE: 13

| ccgtctcgag gctacactta ctttcctggg ttttggcatc gacggttgtg ccttgacttg | 60 |
| gccttaacag acaaattgcc tttgtgttct catctgcagg gtgcacggtg cgaccctggg | 120 |
| cgtgggctcc ctcctggcgg gctttgtggg agaatccacc atggtcgcca tcgctgcgtg | 180 |
| ctatgtctac cggaagcagg tgagacagcc gcgccgggag cctcctcccg ggtgcatcct | 240 |
| cctgggtgca ggagaacctg agcagccact gaccaggttg gatggtggcg ttcg | 294 |

<210> SEQ ID NO 14
<211> LENGTH: 235
<212> TYPE: DNA
<213> ORGANISM: Homo sapiens

<400> SEQUENCE: 14

| gagggtccc ccaagacccc ggtgttgtct ccctgctcgt ggttctgctg tgcagtgtcc | 60 |
| ccatccacag ccccacactg atgagtcttc tttggtctag aaaaagaaga tggagaatga | 120 |

```
gtcggccacg gagggggaag actctgccat gacagacatg cctccgacag aggaggtgac      180
agacatcgtg gaaatgagag aggagaatga ataaggcacg ggacggccat gggca           235

<210> SEQ ID NO 15
<211> LENGTH: 2593
<212> TYPE: DNA
<213> ORGANISM: Mus musculus
<220> FEATURE:
<221> NAME/KEY: misc_feature
<222> LOCATION: (1)...(2593)
<223> OTHER INFORMATION: n = A,T,C or G

<400> SEQUENCE: 15
tgagtgtggg gtcagcccac ggcggggact atggtgaaat tcccggcgct cacgcactac      60
tggcccctga tccggttcct ggtgcccctc ggcatcacca acatagccat cgacttcggg     120
gagcaggcct tgaaccgggg catcgctgca gtcaaggagg atgcagtaga atgctggcc      180 agctacgggc tggcgtattc tttgatgaag ttcttcacgg ggcccatgag tgacttcaaa     240
aatgtgggcc tggtgttcgt gaacagcaag agagacaggg ccaaagccgt cctctgcatg     300
gtggtggccg gtgccatcgc tgccgtcttc cacaccctga tagcctacag tgacttaggg     360
tactacatca tcaacaagct gcatcatgtg gatgagtctg tggggagcaa acacgaagg      420 gccttcctgt atctcgctgc cttcccttt atggatgcca tggcgtggac tcatgctggc      480
attctcttaa aacacaaata cagtttcctg gtgggatgtg cctcaatctc agatgtcata     540
gctcaggttg ttttcgtagc cattttgctt cacagtcacc tggaatgccg agaaccgctg     600
ctcatcccca tcctgtctct gtacatgggt gcgcttgtgc gctgcaccac actgtgcctg     660
ggctactaca ggaacatcca cgacatcatc cccgacagga gcggcccaga gctgggggt     720 gatgcaacca taagaaagat gctgagcttc tggtggcccc tggctctgat cctggccacg     780
cagcgaatca gtcggcccat tgtcaacctc ttcgtgtccc gggaccttgg tggcagctct     840
gctgctacag aggcagtggc cattctgaca gccacctacc ccgtgggtca tatgccatat     900
ggctggttga cagaaatccg ggctgtctac cctgcttttg acaagaataa ccccagcaat     960
aaactggcga acacaagcaa cacggtcacc tcagcccaca tcaagaagtt cacctttgtc    1020
tgcatggcgc tgtcgctgac gctctgtttt gtcatgttct ggaccccaa cgtctctgag    1080 aagattctga tagatatcat tggagtggac tttgcctttg cagaactctg tgtcattcct    1140
ctgcgtatct tctccttctt cccagtgcca gtgactgtga gagctcatct cactggatgg    1200
ctgatgacac tgaagaaaac ctttgtgctg gcgcccagct ccgtgctgcg catcatcgtc    1260
ctcatcacca gccttgtggt cctgccgtac ctgggggtgc acggagccac actaggtgtg    1320
ggctcccttc tagcagggtt tgtgggagaa tctaccatgg ttgcccttgc agcatgctat    1380
gtctatcgaa aacagaaaaa gaagatggag aatgagtcag ccaccgaggg agaagactcg    1440
gccatgaccg acatgcctcc aacagaggag gtcacagaca tcgtagagat gagagaagaa    1500
aatgagtaag cacaggctgc tgggggccac cgcagggaca gtcaggacaa caactgtcgt    1560
ctctttcctc ctcctcctcc catcaagttg ttttctgttg tttaattttt attcttggtt    1620
atgaaagagg ccttgatta gaggtttcgt ataaattctc tagcatactg ggtatgctca    1680
ccgatgcagg gacctgaaga aaggtcttta ctgtcgcttt gtaactcaga atcgctgact    1740
tcacgcccct gcttcataaa acccaaaaga tagagctgcc tcttggtcaa cgtttctact    1800
cccttggaca atctccactt tggaaccaaa ggacttgggc cagactttc ctgttcatgt    1860
```

-continued

```
ttgcctcctc ctaagaatca acaggttgaa gctcagcctc tcttgacttg ctccccaaca    1920
ctgtggctct ggagtcatga actatctgcc gcacatactg gtgggcccca ggctgcagcc    1980
cacagtctcc ctgttcccag aggaagggct ggtggccctg ctgggccaac gtagtgggaa    2040
tttaatctcc tgtagaaatt gggtcagtca ccaactgact tgatcgtcag catcccattg    2100
ttttcctggt ttcactgagt tgccgcaccc cacagtgtat atacatgagc tgacttttca    2160
gagctgtccc gcaagtgcag ctccagtgtc agcaccctcc gcatgagttt ccctgaaggc    2220
ttgcgtttac tcgccttccc tgaagatggc actagagcga gaagtggagc gttntanctg    2280
tccatttctc taactgtcca tttcgttttc acagtgagca agctttaag tcgtaatcta     2340 gcatcctaat gccagggtct tgtctcgtaa cttctgatgt agatgtgccg cctatttctg    2400
caggacaggt aaccgagtgt actatggtac tcccctccac accataaagc aagacatttt    2460
ataaacagta tcaaggtcac tatgtgatac cccggaaata atgcattgga aatccactta    2520
gtgcagtata ttttctaag ttttggaaag cgggtttttt cctttaaaaa aaattatgga     2580
cacagttcac taa                                                      2593
```

<210> SEQ ID NO 16
<211> LENGTH: 492
<212> TYPE: PRT
<213> ORGANISM: Mus musculus

<400> SEQUENCE: 16

```
Met Val Lys Phe Pro Ala Leu Thr His Tyr Trp Pro Leu Ile Arg Phe
  1               5                  10                  15

Leu Val Pro Leu Gly Ile Thr Asn Ile Ala Ile Asp Phe Gly Glu Gln
                 20                  25                  30

Ala Leu Asn Arg Gly Ile Ala Ala Val Lys Glu Asp Ala Val Glu Met
             35                  40                  45

Leu Ala Ser Tyr Gly Leu Ala Tyr Ser Leu Met Lys Phe Phe Thr Gly
         50                  55                  60

Pro Met Ser Asp Phe Lys Asn Val Gly Leu Val Phe Val Asn Ser Lys
 65                  70                  75                  80

Arg Asp Arg Ala Lys Ala Val Leu Cys Met Val Ala Gly Ala Ile
                 85                  90                  95

Ala Ala Val Phe His Thr Leu Ile Ala Tyr Ser Asp Leu Gly Tyr Tyr
                100                 105                 110

Ile Ile Asn Lys Leu His His Val Asp Glu Ser Val Gly Ser Lys Thr
            115                 120                 125

Arg Arg Ala Phe Leu Tyr Leu Ala Ala Phe Pro Phe Met Asp Ala Met
        130                 135                 140

Ala Trp Thr His Ala Gly Ile Leu Leu Lys His Lys Tyr Ser Phe Leu
145                 150                 155                 160

Val Gly Cys Ala Ser Ile Ser Asp Val Ile Ala Gln Val Val Phe Val
                165                 170                 175

Ala Ile Leu Leu His Ser His Leu Glu Cys Arg Glu Pro Leu Leu Ile
            180                 185                 190

Pro Ile Leu Ser Leu Tyr Met Gly Ala Leu Val Arg Cys Thr Thr Leu
        195                 200                 205

Cys Leu Gly Tyr Tyr Arg Asn Ile His Asp Ile Pro Asp Arg Ser
    210                 215                 220

Gly Pro Glu Leu Gly Gly Asp Ala Thr Ile Arg Lys Met Leu Ser Phe
225                 230                 235                 240
```

-continued

```
Trp Trp Pro Leu Ala Leu Ile Leu Ala Thr Gln Arg Ile Ser Arg Pro
                245                 250                 255

Ile Val Asn Leu Phe Val Ser Arg Asp Leu Gly Gly Ser Ser Ala Ala
            260                 265                 270

Thr Glu Ala Val Ala Ile Leu Thr Ala Thr Tyr Pro Val Gly His Met
        275                 280                 285

Pro Tyr Gly Trp Leu Thr Glu Ile Arg Ala Val Tyr Pro Ala Phe Asp
    290                 295                 300

Lys Asn Asn Pro Ser Asn Lys Leu Ala Asn Thr Ser Asn Thr Val Thr
305                 310                 315                 320

Ser Ala His Ile Lys Lys Phe Thr Phe Val Cys Met Ala Leu Ser Leu
                325                 330                 335

Thr Leu Cys Phe Val Met Phe Trp Thr Pro Asn Val Ser Glu Lys Ile
            340                 345                 350

Leu Ile Asp Ile Ile Gly Val Asp Phe Ala Phe Ala Glu Leu Cys Val
        355                 360                 365

Ile Pro Leu Arg Ile Phe Ser Phe Pro Val Pro Val Thr Val Arg
    370                 375                 380

Ala His Leu Thr Gly Trp Leu Met Thr Leu Lys Lys Thr Phe Val Leu
385                 390                 395                 400

Ala Pro Ser Ser Val Leu Arg Ile Ile Val Leu Ile Thr Ser Leu Val
                405                 410                 415

Val Leu Pro Tyr Leu Gly Val His Gly Ala Thr Leu Gly Val Gly Ser
            420                 425                 430

Leu Leu Ala Gly Phe Val Gly Glu Ser Thr Met Val Ala Leu Ala Ala
        435                 440                 445

Cys Tyr Val Tyr Arg Lys Gln Lys Lys Lys Met Glu Asn Glu Ser Ala
    450                 455                 460

Thr Glu Gly Glu Asp Ser Ala Met Thr Asp Met Pro Pro Thr Glu Glu
465                 470                 475                 480

Val Thr Asp Ile Val Glu Met Arg Glu Glu Asn Glu
                485                 490
```

```
<210> SEQ ID NO 17
<211> LENGTH: 31
<212> TYPE: DNA
<213> ORGANISM: Artificial Sequence
<220> FEATURE:
<223> OTHER INFORMATION: synthesized primer

<400> SEQUENCE: 17
aaaacgacgg ccagtgaatt gtaatacgac t                              31

<210> SEQ ID NO 18
<211> LENGTH: 31
<212> TYPE: DNA
<213> ORGANISM: Artificial Sequence
<220> FEATURE:
<223> OTHER INFORMATION: synthesized primer

<400> SEQUENCE: 18
catgattacg ccaagctatt taggtgacac t                              31

<210> SEQ ID NO 19
<211> LENGTH: 19
<212> TYPE: DNA
<213> ORGANISM: Artificial Sequence
<220> FEATURE:
<223> OTHER INFORMATION: synthesized primer
```

```
<400> SEQUENCE: 19
aattaaccct cactaaagg                                          19

<210> SEQ ID NO 20
<211> LENGTH: 20
<212> TYPE: DNA
<213> ORGANISM: Artificial Sequence
<220> FEATURE:
<223> OTHER INFORMATION: synthesized primer

<400> SEQUENCE: 20
gtaatacgac tcactatagg                                         20

<210> SEQ ID NO 21
<211> LENGTH: 22
<212> TYPE: DNA
<213> ORGANISM: Artificial Sequence
<220> FEATURE:
<223> OTHER INFORMATION: synthesized primer

<400> SEQUENCE: 21
taggaaatgt attatagcct aa                                      22

<210> SEQ ID NO 22
<211> LENGTH: 20
<212> TYPE: DNA
<213> ORGANISM: Artificial Sequence
<220> FEATURE:
<223> OTHER INFORMATION: synthesized primer

<400> SEQUENCE: 22
tgagtgtggg gtcagcccac                                         20

<210> SEQ ID NO 23
<211> LENGTH: 21
<212> TYPE: DNA
<213> ORGANISM: Artificial Sequence
<220> FEATURE:
<223> OTHER INFORMATION: synthesized primer

<400> SEQUENCE: 23
actttgacta aatcaggaat t                                       21

<210> SEQ ID NO 24
<211> LENGTH: 21
<212> TYPE: DNA
<213> ORGANISM: Artificial Sequence
<220> FEATURE:
<223> OTHER INFORMATION: synthesized primer

<400> SEQUENCE: 24
tagtgaactg tgtccataat t                                       21

<210> SEQ ID NO 25
<211> LENGTH: 20
<212> TYPE: DNA
<213> ORGANISM: Artificial Sequence
<220> FEATURE:
<223> OTHER INFORMATION: synthesized primer

<400> SEQUENCE: 25
gggtactaca tcatcaacaa                                         20

<210> SEQ ID NO 26
```

```
<210> SEQ ID NO 26
<211> LENGTH: 20
<212> TYPE: DNA
<213> ORGANISM: Artificial Sequence
<220> FEATURE:
<223> OTHER INFORMATION: synthesized primer

<400> SEQUENCE: 26
tggctctgat cctggccacg                                               20

<210> SEQ ID NO 27
<211> LENGTH: 20
<212> TYPE: DNA
<213> ORGANISM: Artificial Sequence
<220> FEATURE:
<223> OTHER INFORMATION: synthesized primer

<400> SEQUENCE: 27
ccagtgccag tgactgtgag                                               20

<210> SEQ ID NO 28
<211> LENGTH: 20
<212> TYPE: DNA
<213> ORGANISM: Artificial Sequence
<220> FEATURE:
<223> OTHER INFORMATION: synthesized primer

<400> SEQUENCE: 28
gtcaggacaa caactgtcgt                                               20

<210> SEQ ID NO 29
<211> LENGTH: 20
<212> TYPE: DNA
<213> ORGANISM: Artificial Sequence
<220> FEATURE:
<223> OTHER INFORMATION: synthesized primer

<400> SEQUENCE: 29
aactatctgc cgcacatact                                               20

<210> SEQ ID NO 30
<211> LENGTH: 20
<212> TYPE: DNA
<213> ORGANISM: Artificial Sequence
<220> FEATURE:
<223> OTHER INFORMATION: synthesized primer

<400> SEQUENCE: 30
tgccagggtc ttgtctcgta                                               20

<210> SEQ ID NO 31
<211> LENGTH: 20
<212> TYPE: DNA
<213> ORGANISM: Artificial Sequence
<220> FEATURE:
<223> OTHER INFORMATION: synthesized primer

<400> SEQUENCE: 31
aacgaaatgg acagttagag                                               20

<210> SEQ ID NO 32
<211> LENGTH: 20
<212> TYPE: DNA
<213> ORGANISM: Artificial Sequence
<220> FEATURE:
<223> OTHER INFORMATION: synthesized primer

<400> SEQUENCE: 32
```
ggagcaagtc aagagaggct                                                    20

<210> SEQ ID NO 33
<211> LENGTH: 20
<212> TYPE: DNA
<213> ORGANISM: Artificial Sequence
<220> FEATURE:
<223> OTHER INFORMATION: synthesized primer

<400> SEQUENCE: 33
gcagcctgtg cttactcatt                                                    20

<210> SEQ ID NO 34
<211> LENGTH: 20
<212> TYPE: DNA
<213> ORGANISM: Artificial Sequence
<220> FEATURE:
<223> OTHER INFORMATION: synthesized primer

<400> SEQUENCE: 34
ggcaaagtcc actccaatga                                                    20

<210> SEQ ID NO 35
<211> LENGTH: 20
<212> TYPE: DNA
<213> ORGANISM: Artificial Sequence
<220> FEATURE:
<223> OTHER INFORMATION: synthesized primer

<400> SEQUENCE: 35
cagctctggg ccgctcctgt                                                    20

<210> SEQ ID NO 36
<211> LENGTH: 20
<212> TYPE: DNA
<213> ORGANISM: Artificial Sequence
<220> FEATURE:
<223> OTHER INFORMATION: synthesized primer

<400> SEQUENCE: 36
tcagggtgtg gaagacggca                                                    20

<210> SEQ ID NO 37
<211> LENGTH: 20
<212> TYPE: DNA
<213> ORGANISM: Artificial Sequence
<220> FEATURE:
<223> OTHER INFORMATION: synthesized primer

<400> SEQUENCE: 37
ggctcccttc tagcagggtt                                                    20

<210> SEQ ID NO 38
<211> LENGTH: 20
<212> TYPE: DNA
<213> ORGANISM: Artificial Sequence
<220> FEATURE:
<223> OTHER INFORMATION: synthesized primer

<400> SEQUENCE: 38
agcatgctgc aagggcaacc                                                    20

<210> SEQ ID NO 39
<211> LENGTH: 22
<212> TYPE: DNA

```
<213> ORGANISM: Artificial Sequence
<220> FEATURE:
<223> OTHER INFORMATION: synthesized primer

<400> SEQUENCE: 39
tgtagccatt ttgcttcaca gt                                              22

<210> SEQ ID NO 40
<211> LENGTH: 19
<212> TYPE: DNA
<213> ORGANISM: Artificial Sequence
<220> FEATURE:
<223> OTHER INFORMATION: synthesized primer

<400> SEQUENCE: 40
agctcggggc cacttctgt                                                  19

<210> SEQ ID NO 41
<211> LENGTH: 20
<212> TYPE: DNA
<213> ORGANISM: Artificial Sequence
<220> FEATURE:
<223> OTHER INFORMATION: synthesized primer

<400> SEQUENCE: 41
gcattgctgc tgtcaaggag                                                 20

<210> SEQ ID NO 42
<211> LENGTH: 20
<212> TYPE: DNA
<213> ORGANISM: Artificial Sequence
<220> FEATURE:
<223> OTHER INFORMATION: synthesized primer

<400> SEQUENCE: 42
tgctgttcac aaacaccagg                                                 20

<210> SEQ ID NO 43
<211> LENGTH: 30
<212> TYPE: DNA
<213> ORGANISM: Artificial Sequence
<220> FEATURE:
<223> OTHER INFORMATION: synthesized primer

<400> SEQUENCE: 43
cgaatcgtaa ccgttcgtac gagaatcgct                                      30

<210> SEQ ID NO 44
<211> LENGTH: 18
<212> TYPE: DNA
<213> ORGANISM: Artificial Sequence
<220> FEATURE:
<223> OTHER INFORMATION: synthesized primer

<400> SEQUENCE: 44
gtaaaacgac ggccagtg                                                   18

<210> SEQ ID NO 45
<211> LENGTH: 19
<212> TYPE: DNA
<213> ORGANISM: Artificial Sequence
<220> FEATURE:
<223> OTHER INFORMATION: synthesized primer

<400> SEQUENCE: 45
ggaaacagct atgaccatg                                                  19
```

<210> SEQ ID NO 46
<211> LENGTH: 20
<212> TYPE: DNA
<213> ORGANISM: Artificial Sequence
<220> FEATURE:
<223> OTHER INFORMATION: synthesized primer

<400> SEQUENCE: 46
agcaagacga gaagggcctt                                              20

<210> SEQ ID NO 47
<211> LENGTH: 20
<212> TYPE: DNA
<213> ORGANISM: Artificial Sequence
<220> FEATURE:
<223> OTHER INFORMATION: synthesized primer

<400> SEQUENCE: 47
aaggcccttc tcgtcttgct                                              20

<210> SEQ ID NO 48
<211> LENGTH: 20
<212> TYPE: DNA
<213> ORGANISM: Artificial Sequence
<220> FEATURE:
<223> OTHER INFORMATION: synthesized primer

<400> SEQUENCE: 48
gacccatgct ggcattctct                                              20

<210> SEQ ID NO 49
<211> LENGTH: 20
<212> TYPE: DNA
<213> ORGANISM: Artificial Sequence
<220> FEATURE:
<223> OTHER INFORMATION: synthesized primer

<400> SEQUENCE: 49
atgacatctg agattgaggc                                              20

<210> SEQ ID NO 50
<211> LENGTH: 26
<212> TYPE: DNA
<213> ORGANISM: Artificial Sequence
<220> FEATURE:
<223> OTHER INFORMATION: synthesized primer

<400> SEQUENCE: 50
ctggctacta caagaacatt cacgac                                       26

<210> SEQ ID NO 51
<211> LENGTH: 25
<212> TYPE: DNA
<213> ORGANISM: Artificial Sequence
<220> FEATURE:
<223> OTHER INFORMATION: synthesized primer

<400> SEQUENCE: 51
cacttctgtc agggatgatg tcgtg                                        25

<210> SEQ ID NO 52
<211> LENGTH: 25
<212> TYPE: DNA
<213> ORGANISM: Artificial Sequence
<220> FEATURE:

```
<223> OTHER INFORMATION: synthesized primer

<400> SEQUENCE: 52
gcgattttga cagccacata ccctg                                          25

<210> SEQ ID NO 53
<211> LENGTH: 25
<212> TYPE: DNA
<213> ORGANISM: Artificial Sequence
<220> FEATURE:
<223> OTHER INFORMATION: synthesized primer

<400> SEQUENCE: 53
ttgtcgaaag caggatacac agcac                                          25

<210> SEQ ID NO 54
<211> LENGTH: 26
<212> TYPE: DNA
<213> ORGANISM: Artificial Sequence
<220> FEATURE:
<223> OTHER INFORMATION: synthesized primer

<400> SEQUENCE: 54
aaccccagca acaaactggt gagcac                                         26

<210> SEQ ID NO 55
<211> LENGTH: 26
<212> TYPE: DNA
<213> ORGANISM: Artificial Sequence
<220> FEATURE:
<223> OTHER INFORMATION: synthesized primer

<400> SEQUENCE: 55
tgagtgacag agccatgcag acgaag                                         26

<210> SEQ ID NO 56
<211> LENGTH: 25
<212> TYPE: DNA
<213> ORGANISM: Artificial Sequence
<220> FEATURE:
<223> OTHER INFORMATION: synthesized primer

<400> SEQUENCE: 56
ctgtttcgtg atgttttgga caccc                                          25

<210> SEQ ID NO 57
<211> LENGTH: 25
<212> TYPE: DNA
<213> ORGANISM: Artificial Sequence
<220> FEATURE:
<223> OTHER INFORMATION: synthesized primer

<400> SEQUENCE: 57
tggaactggg aagaaggaga agatc                                          25

<210> SEQ ID NO 58
<211> LENGTH: 20
<212> TYPE: DNA
<213> ORGANISM: Artificial Sequence
<220> FEATURE:
<223> OTHER INFORMATION: synthesized primer

<400> SEQUENCE: 58
caattaaccc tcactaaagg                                                20
```

<210> SEQ ID NO 59
<211> LENGTH: 18
<212> TYPE: DNA
<213> ORGANISM: Artificial Sequence
<220> FEATURE:
<223> OTHER INFORMATION: synthesized primer

<400> SEQUENCE: 59
gtaatacgac tcactata                                                18

<210> SEQ ID NO 60
<211> LENGTH: 20
<212> TYPE: DNA
<213> ORGANISM: Artificial Sequence
<220> FEATURE:
<223> OTHER INFORMATION: synthesized primer

<400> SEQUENCE: 60
aaggcccttc tcgtcttgct                                              20

<210> SEQ ID NO 61
<211> LENGTH: 21
<212> TYPE: DNA
<213> ORGANISM: Artificial Sequence
<220> FEATURE:
<223> OTHER INFORMATION: synthesized primer

<400> SEQUENCE: 61
tccttgacag cagcaatgcc c                                            21

<210> SEQ ID NO 62
<211> LENGTH: 23
<212> TYPE: DNA
<213> ORGANISM: Artificial Sequence
<220> FEATURE:
<223> OTHER INFORMATION: synthesized primer

<400> SEQUENCE: 62
acagcaatgc cccggttcaa ggc                                          23

<210> SEQ ID NO 63
<211> LENGTH: 22
<212> TYPE: DNA
<213> ORGANISM: Artificial Sequence
<220> FEATURE:
<223> OTHER INFORMATION: synthesized primer

<400> SEQUENCE: 63
aactgaagct gatgtagatg aa                                           22

<210> SEQ ID NO 64
<211> LENGTH: 21
<212> TYPE: DNA
<213> ORGANISM: Artificial Sequence
<220> FEATURE:
<223> OTHER INFORMATION: synthesized primer

<400> SEQUENCE: 64
atcgctgtcc tctccttaaa t                                            21

<210> SEQ ID NO 65
<211> LENGTH: 23
<212> TYPE: DNA
<213> ORGANISM: Artificial Sequence
<220> FEATURE:
<223> OTHER INFORMATION: synthesized primer -continued

```
<400> SEQUENCE: 65
aaccaatcac ctttatccaa tta                                             23

<210> SEQ ID NO 66
<211> LENGTH: 21
<212> TYPE: DNA
<213> ORGANISM: Artificial Sequence
<220> FEATURE:
<223> OTHER INFORMATION: synthesized primer

<400> SEQUENCE: 66
ttgccaaagc tagattcgtc a                                               21

<210> SEQ ID NO 67
<211> LENGTH: 22
<212> TYPE: DNA
<213> ORGANISM: Artificial Sequence
<220> FEATURE:
<223> OTHER INFORMATION: synthesized primer

<400> SEQUENCE: 67
caccagatca agttacagta at                                              22

<210> SEQ ID NO 68
<211> LENGTH: 22
<212> TYPE: DNA
<213> ORGANISM: Artificial Sequence
<220> FEATURE:
<223> OTHER INFORMATION: synthesized primer

<400> SEQUENCE: 68
atactgttat tacagggcat tc                                              22

<210> SEQ ID NO 69
<211> LENGTH: 22
<212> TYPE: DNA
<213> ORGANISM: Artificial Sequence
<220> FEATURE:
<223> OTHER INFORMATION: synthesized primer

<400> SEQUENCE: 69
caccagatca agttacagta at                                              22

<210> SEQ ID NO 70
<211> LENGTH: 20
<212> TYPE: DNA
<213> ORGANISM: Artificial Sequence
<220> FEATURE:
<223> OTHER INFORMATION: synthesized primer

<400> SEQUENCE: 70
tgatgtaacg gtgctggcaa                                                 20

<210> SEQ ID NO 71
<211> LENGTH: 22
<212> TYPE: DNA
<213> ORGANISM: Artificial Sequence
<220> FEATURE:
<223> OTHER INFORMATION: synthesized primer

<400> SEQUENCE: 71
tcatggtggg tataacaaaa tg                                              22

<210> SEQ ID NO 72
<211> LENGTH: 20
```

```
<212> TYPE: DNA
<213> ORGANISM: Artificial Sequence
<220> FEATURE:
<223> OTHER INFORMATION: synthesized primer

<400> SEQUENCE: 72
ttccctgcag acatctagca                                            20

<210> SEQ ID NO 73
<211> LENGTH: 20
<212> TYPE: DNA
<213> ORGANISM: Artificial Sequence
<220> FEATURE:
<223> OTHER INFORMATION: synthesized primer

<400> SEQUENCE: 73
ccatgttcct ccagtgaatc                                            20

<210> SEQ ID NO 74
<211> LENGTH: 20
<212> TYPE: DNA
<213> ORGANISM: Artificial Sequence
<220> FEATURE:
<223> OTHER INFORMATION: synthesized primer

<400> SEQUENCE: 74
atgacatcct ggccaacttc                                            20

<210> SEQ ID NO 75
<211> LENGTH: 20
<212> TYPE: DNA
<213> ORGANISM: Artificial Sequence
<220> FEATURE:
<223> OTHER INFORMATION: synthesized primer

<400> SEQUENCE: 75
gttcgtacga gaatcgctgt                                            20

<210> SEQ ID NO 76
<211> LENGTH: 19
<212> TYPE: DNA
<213> ORGANISM: Artificial Sequence
<220> FEATURE:
<223> OTHER INFORMATION: synthesized primer

<400> SEQUENCE: 76
catcctggga tcagcgtca                                             19

<210> SEQ ID NO 77
<211> LENGTH: 19
<212> TYPE: DNA
<213> ORGANISM: Artificial Sequence
<220> FEATURE:
<223> OTHER INFORMATION: synthesized primer

<400> SEQUENCE: 77
ttgtcaccca gtgtagcgg                                             19

<210> SEQ ID NO 78
<211> LENGTH: 22
<212> TYPE: DNA
<213> ORGANISM: Artificial Sequence
<220> FEATURE:
<223> OTHER INFORMATION: synthesized primer

<400> SEQUENCE: 78
```

-continued

| | |
|---|---|
| caacgtcaca ttaaccttac aa | 22 |

<210> SEQ ID NO 79
<211> LENGTH: 21
<212> TYPE: DNA
<213> ORGANISM: Artificial Sequence
<220> FEATURE:
<223> OTHER INFORMATION: synthesized primer

<400> SEQUENCE: 79

| | |
|---|---|
| ctacacttac tttcctgggt t | 21 |

<210> SEQ ID NO 80
<211> LENGTH: 19
<212> TYPE: DNA
<213> ORGANISM: Artificial Sequence
<220> FEATURE:
<223> OTHER INFORMATION: synthesized primer

<400> SEQUENCE: 80

| | |
|---|---|
| cagtggctgc tcaggttct | 19 |

<210> SEQ ID NO 81
<211> LENGTH: 19
<212> TYPE: DNA
<213> ORGANISM: Artificial Sequence
<220> FEATURE:
<223> OTHER INFORMATION: synthesized primer

<400> SEQUENCE: 81

| | |
|---|---|
| catcgacggt tgtgccttg | 19 |

<210> SEQ ID NO 82
<211> LENGTH: 18
<212> TYPE: DNA
<213> ORGANISM: Artificial Sequence
<220> FEATURE:
<223> OTHER INFORMATION: synthesized primer

<400> SEQUENCE: 82

| | |
|---|---|
| ctgcacccag gaggatgc | 18 |

<210> SEQ ID NO 83
<211> LENGTH: 21
<212> TYPE: DNA
<213> ORGANISM: Artificial Sequence
<220> FEATURE:
<223> OTHER INFORMATION: synthesized primer

<400> SEQUENCE: 83

| | |
|---|---|
| gaaggtttaa gcctacagtg a | 21 |

<210> SEQ ID NO 84
<211> LENGTH: 20
<212> TYPE: DNA
<213> ORGANISM: Artificial Sequence
<220> FEATURE:
<223> OTHER INFORMATION: synthesized primer

<400> SEQUENCE: 84

| | |
|---|---|
| tgatgccgaa gtgtcatcct | 20 |

<210> SEQ ID NO 85
<211> LENGTH: 21
<212> TYPE: DNA
<213> ORGANISM: Artificial Sequence

```
<220> FEATURE:
<223> OTHER INFORMATION: synthesized primer

<400> SEQUENCE: 85
gaaggtttaa gcctacagtg a                                              21

<210> SEQ ID NO 86
<211> LENGTH: 19
<212> TYPE: DNA
<213> ORGANISM: Artificial Sequence
<220> FEATURE:
<223> OTHER INFORMATION: synthesized primer

<400> SEQUENCE: 86
gactgactgt ccctgcagt                                                 19

<210> SEQ ID NO 87
<211> LENGTH: 22
<212> TYPE: DNA
<213> ORGANISM: Artificial Sequence
<220> FEATURE:
<223> OTHER INFORMATION: synthesized primer

<400> SEQUENCE: 87
gatgagattg tagatgattt tt                                             22

<210> SEQ ID NO 88
<211> LENGTH: 23
<212> TYPE: DNA
<213> ORGANISM: Artificial Sequence
<220> FEATURE:
<223> OTHER INFORMATION: synthesized primer

<400> SEQUENCE: 88
ctatgacgaa caaatactac att                                            23

<210> SEQ ID NO 89
<211> LENGTH: 20
<212> TYPE: DNA
<213> ORGANISM: Artificial Sequence
<220> FEATURE:
<223> OTHER INFORMATION: synthesized primer

<400> SEQUENCE: 89
aagccaacga tcttctctac                                                20

<210> SEQ ID NO 90
<211> LENGTH: 20
<212> TYPE: DNA
<213> ORGANISM: Artificial Sequence
<220> FEATURE:
<223> OTHER INFORMATION: synthesized primer

<400> SEQUENCE: 90
gcttccagcc agtccatttg                                                20

<210> SEQ ID NO 91
<211> LENGTH: 19
<212> TYPE: DNA
<213> ORGANISM: Artificial Sequence
<220> FEATURE:
<223> OTHER INFORMATION: synthesized primer

<400> SEQUENCE: 91
atcataagcc ccacatccc                                                 19
```

<210> SEQ ID NO 92
<211> LENGTH: 20
<212> TYPE: DNA
<213> ORGANISM: Artificial Sequence
<220> FEATURE:
<223> OTHER INFORMATION: synthesized primer

<400> SEQUENCE: 92
ttggttagag attccccgag                                                    20

<210> SEQ ID NO 93
<211> LENGTH: 20
<212> TYPE: DNA
<213> ORGANISM: Artificial Sequence
<220> FEATURE:
<223> OTHER INFORMATION: synthesized primer

<400> SEQUENCE: 93
tcaacatgac agcccgcttg                                                    20

<210> SEQ ID NO 94
<211> LENGTH: 23
<212> TYPE: DNA
<213> ORGANISM: Artificial Sequence
<220> FEATURE:
<223> OTHER INFORMATION: synthesized primer

<400> SEQUENCE: 94
tgagaagtcc caagaaatgc ctg                                                23

<210> SEQ ID NO 95
<211> LENGTH: 21
<212> TYPE: DNA
<213> ORGANISM: Artificial Sequence
<220> FEATURE:
<223> OTHER INFORMATION: synthesized primer

<400> SEQUENCE: 95
cggttgtccc tctttcgtaa c                                                  21

<210> SEQ ID NO 96
<211> LENGTH: 22
<212> TYPE: DNA
<213> ORGANISM: Artificial Sequence
<220> FEATURE:
<223> OTHER INFORMATION: synthesized primer

<400> SEQUENCE: 96
ggcatgagga taaacaggaa tg                                                 22

<210> SEQ ID NO 97
<211> LENGTH: 20
<212> TYPE: DNA
<213> ORGANISM: Artificial Sequence
<220> FEATURE:
<223> OTHER INFORMATION: synthesized primer

<400> SEQUENCE: 97
gccagcggtt caaaaaaaag                                                    20

<210> SEQ ID NO 98
<211> LENGTH: 19
<212> TYPE: DNA
<213> ORGANISM: Artificial Sequence
<220> FEATURE:
<223> OTHER INFORMATION: synthesized primer

```
<400> SEQUENCE: 98
agacgtgcct ggggatttc                                              19

<210> SEQ ID NO 99
<211> LENGTH: 19
<212> TYPE: DNA
<213> ORGANISM: Artificial Sequence
<220> FEATURE:
<223> OTHER INFORMATION: synthesized primer

<400> SEQUENCE: 99
tgtgaatgta cttcctgcc                                              19

<210> SEQ ID NO 100
<211> LENGTH: 22
<212> TYPE: DNA
<213> ORGANISM: Artificial Sequence
<220> FEATURE:
<223> OTHER INFORMATION: synthesized primer

<400> SEQUENCE: 100
gtcccaagaa atgcctgaag tg                                          22

<210> SEQ ID NO 101
<211> LENGTH: 23
<212> TYPE: DNA
<213> ORGANISM: Artificial Sequence
<220> FEATURE:
<223> OTHER INFORMATION: synthesized primer

<400> SEQUENCE: 101
gccacacctg atctgctcaa ttc                                         23

<210> SEQ ID NO 102
<211> LENGTH: 21
<212> TYPE: DNA
<213> ORGANISM: Artificial Sequence
<220> FEATURE:
<223> OTHER INFORMATION: synthesized primer

<400> SEQUENCE: 102
gatttcccct gaaaatgtag c                                           21

<210> SEQ ID NO 103
<211> LENGTH: 21
<212> TYPE: DNA
<213> ORGANISM: homo sapiens

<400> SEQUENCE: 103
ccatcgctgc cgtctttcac a                                           21

<210> SEQ ID NO 104
<211> LENGTH: 21
<212> TYPE: DNA
<213> ORGANISM: homo sapiens

<400> SEQUENCE: 104
ccatcgctgc tgtctttcac a                                           21

<210> SEQ ID NO 105
<211> LENGTH: 21
<212> TYPE: DNA
<213> ORGANISM: homo sapiens
```

```
<400> SEQUENCE: 105
aggtgaggcc gccgaccgcc a                                              21

<210> SEQ ID NO 106
<211> LENGTH: 21
<212> TYPE: DNA
<213> ORGANISM: homo sapiens

<400> SEQUENCE: 106
aggtgaggcc accgaccgcc a                                              21

<210> SEQ ID NO 107
<211> LENGTH: 21
<212> TYPE: DNA
<213> ORGANISM: homo sapiens

<400> SEQUENCE: 107
gcttctgtca gtcggttccc g                                              21

<210> SEQ ID NO 108
<211> LENGTH: 21
<212> TYPE: DNA
<213> ORGANISM: homo sapeins

<400> SEQUENCE: 108
gcttctgtca atcggttccc g                                              21

<210> SEQ ID NO 109
<211> LENGTH: 21
<212> TYPE: DNA
<213> ORGANISM: homo sapiens

<400> SEQUENCE: 109
cagtcacggc agcccacatc a                                              21

<210> SEQ ID NO 110
<211> LENGTH: 21
<212> TYPE: DNA
<213> ORGANISM: homo sapiens

<400> SEQUENCE: 110
cagtcacggc ggcccacatc a                                              21

<210> SEQ ID NO 111
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 111
catcggtacc gcttatatgg                                                20

<210> SEQ ID NO 112
<211> LENGTH: 20
<212> TYPE: DNA
<213> ORGANISM: Artificial Sequence
<220> FEATURE:
<223> OTHER INFORMATION: synthesized primer

<400> SEQUENCE: 112
accattttcc agagagggct                                                20
```

```
<210> SEQ ID NO 113
<211> LENGTH: 21
<212> TYPE: DNA
<213> ORGANISM: homo sapiens

<400> SEQUENCE: 113
gtctacagac acttttcctt a                                              21

<210> SEQ ID NO 114
<211> LENGTH: 21
<212> TYPE: DNA
<213> ORGANISM: homo sapiens

<400> SEQUENCE: 114
gtctacagac gcttttcctt a                                              21
```

GENE INVOLVED IN MINERAL DEPOSITION AND USES THEREOF

CROSS REFERENCE

This application claims priority to U.S. Provisional Patent Application Ser. No. 60/174,640, filed Jan. 5, 2000, which is incorporated herein by reference in its entirety.

GOVERNMENT RIGHTS

The United States Government may have certain rights in this application pursuant to Grant No. 5T32GM07365 awarded by the National Institutes of Health.

FIELD OF THE INVENTION

This invention relates to nucleic acids encoding a gene controlling mineral deposition and susceptibility to arthritis, proteins encoded by such nucleic acids, compounds containing such nucleic acids and proteins, and methods involving use of these nucleic acids and/or proteins.

BACKGROUND OF THE INVENTION

Arthritis and other rheumatologic disorders are among the most common human health afflictions. In the United States, they are more prevalent and a more common cause of disability than either heart disease or cancer (Lawrence et al., *J. Rheumatol.*, 16:427–41 (1989)). Epidemiological surveys estimate that over 40 million people in this country alone are afflicted with arthritis, accounting for some 315 million physician visits per year (Yelin and Felts, *Arthritis Rheum.*, 33:750–5 (1990)). The economic cost that arthritis extracts on the nation is equally enormous—over $100 billion per year in medical costs and lost productivity (Yelin and Callahan, *Arthritis Rheum.*, 38:1351–62 (1995)). With a demographic of an aging population, the health and economic tolls of arthritis and other musculoskeletal disorders are predicted to increase even more dramatically in the years to come.

Arthritis, which literally means "inflammation of the joint," is a broad clinical term that is used to describe an array of rheumatologic conditions that commonly present with pain, swelling, and stiffness in the joints that may progress to deformity and loss of mobility in severe cases. Based on various clinical, radiologic, and laboratory criteria, clinicians have further divided arthritic disorders into different types. The most common type of arthritis is Osteoarthritis (OA) (Lawrence, J., *Rheumatisms in populations*, London: William Heinemann Medical Books, (1977)). OA affects people of all ages and ethnicities, with a peak prevalence of 80% among people over 65 (Moskowitz, R. W., *Am. J. Med.*, 83:5–10 (1987)). Joints commonly involved include the hips, knees, and finger joints of the hand as well as the weight-bearing joints in the vertebral column. Cardinal features of OA include chondrocyte hyperplasia and necrosis, cartilage destruction, osteophyte and bony, cyst formation, joint space narrowing, and the presence of debris in the joint space that may ultimately lead to the formation of a synovial pannus that bridges the entire joint, rendering it immobile. Although its name implies a central role for inflammation in its pathogenesis, the inflammatory process is not prominent in most cases of OA and may be present in some cases as a secondary phenomenon of joint destruction.

Besides OA, other common types of arthritis include crystal arthropathies, rheumatoid arthritis, spondyloarthropathies, infectious arthritis, and others. Each of these types of arthritis is characterized by a set of clinical and pathological features (e.g. mineral deposits in crystal arthropathies, chronic inflammation and autoimmune reactions in rheumatoid arthritis, etc.), though these features may not necessarily be specific to a particular subtype of arthritis. For example, the mineral deposits in affected joints in crystal arthropathies are often found in other forms of arthritis such as OA. The high prevalence of crystal deposits and synovial fluid crystals in patients presenting with symptoms of OA suggests that crystal deposition may be a causal or contributing factor to the clinical entity normally termed OA (Huskisson et al., *Ann. Rheum. Dis.*, 38:423–8 (1979); Ledingham et al., *Ann. Rheum. Dis.*, 52:520–6 (1993); Gerster, J. C., *J Rheumatol.*, 21:2164–5 (1994); Fam, A. G., *Curr. Opin. Rheumatol*, 7:364–8 (1995)).

Despite the tremendous individual and social impact of arthritis, very little is currently known about the underlying etiology of these disorders. While twin and family studies have identified a strong hereditary component for many arthritic disorders, other studies have also reported links to weight, occupation, presence of prior joint injuries as well as other metabolic and endocrine diseases (Klippel and Dieppe, *Rheumatology* (2nd Ed.), London: Mosby, (1998)). This poor understanding of arthritic diseases is reflected in the limited therapy options available for arthritic patients today. The mainstay in anti-arthritic therapy today consists of the clinical management of symptoms with pain medication, dietary supplements, and exercise. Unfortunately none of these treatments are very effective in slowing the progression of the disease, and patients that are in advanced stages of the disease often require joint replacement and bone fusion surgeries (Klippel and Dieppe, supra).

A spontaneous mouse mutation called progressive ankylosis (ank) was described several years ago that causes abnormal calcium deposition in many skeletal elements, enlargement and fusion of many small bones, and new bone and cartilage formation that bridges all synovial joints in the skeleton (Sweet and Green, *J Hered.*, 72:87–93 (1981)). Mice homozygous for the mutation show progressive loss of mobility that begins in the distal limbs, and later spreads to include many joints in the limbs, sternum, and vertebral column. Histological, EM, and X-ray diffraction studies suggest that the earliest changes in the animals are increased depositions of calcium hydroxyapatite in bones, cartilage, and synovial joints, leading to wider and thicker bones (Hakim et al., *Arthritis Rheum.*, 27:1411–20 (1984); Sampson, H. W., *Am. J Anat.*, 182:257–69 (1988); Sampson, H. W., *Spine*, 13:645–9 (1988); Mahowald et al., *J. Rheumatol.*, 16:60–6 (1989); Sampson et al., *Acta Anat.* (*Basel*), 141:36–41 (1991)). Increased mineral levels in joints are thought to trigger proliferative changes in the synovium and ectopic formation of cartilage and bone in and around joints (Hakim et al., *Arthritis Rheum.*, 29:114–23 (1986)).

The ank mouse mutation provides an important model system for studying genetic predisposition to ectopic mineral deposition and arthritis in humans. Several human joint syndromes are known that show clear autosomal inheritance and a clinical presentation of joint pain, chondrocalcinosis, osteoarthritis, or pseudo rheumatoid arthritis, often requiring hip or knee replacements of affected individuals in their twenties or thirties (Baldwin et al., *Am. J. Hum. Genet.*, 56:692–7 (1995); Hughes et al., *Hum. Mol. Genet.*, 4:1225–8 (1995); Andrew et al., *Am. J. Hum. Genet.*, 64:136–45 (1999)). Like the ank mutation, these human syndromes are associated with increased mineral deposition in bone and cartilage elements. In addition, 30% or more of the elderly human population show increased deposition of mineral in cartilage and bone elements (Felson et al., *J Rheumatol.*, 16:1241–5 (1989)). Increased mineral deposition doubles the risk of developing osteoarthritis, which is one of the major causes of morbidity and decreased activity and a major reason for consulting doctors and taking medications in both young and elderly populations (Felson et al., *J Rheumatol.*, 16:1241–5 (1989); Badley et al., *J Rheumatol*, 21:505–14 (1994)).

Although the ank mutation was first reported in 1981, nothing is known about the molecular nature of the ank gene product. Isolation of this gene will lead to important new understanding of the mechanisms that control mineral deposition, osteophyte formation, and genetic susceptibility to osteoarthritis in both mice and humans. In addition, identification of the normal product of the gene may suggest new treatments or drug targets that can be used to modulate levels of mineral deposition and osteoarthritis in millions of human patients.

There is a need for the identification and determination of a gene associated with arthritis. Identification of such a gene will allow advances in the diagnosis, prognosis, and therapy of arthritis.

SUMMARY OF THE INVENTION

The present invention features a novel human protein (ANK) and nucleotide sequences encoding human ANK. In a particular aspect, the polynucleotide is the nucleotide sequence of SEQ ID NO:1, and more particularly the open reading frame of residues 71–1549. In related aspects the invention features expression vectors and host cells comprising polynucleotides that encode a human ANK (e.g., a human ANK polypeptide having the amino acid sequence of SEQ ID NO:2). The present invention also relates to antibodies that bind specifically to a human ANK, and methods for producing human ANK polypeptides.

A primary object of the invention is to provide an isolated human ANK-encoding polynucleotide for use in expression of human ANK (e.g., in a recombinant host cell) and for use in, for example, identification of human ANK-binding compounds (especially those compounds that affect human ANK-mediated activity, and compounds that can be used to modulate ANK activity).

Another object of the invention is to provide an ANK-based therapeutic, e.g., an agent that modulates ANK-mediated in vivo activities, and screening methods to identify such ANK-modulating agents.

Agents that decrease ANK expression and/or activity are useful in enhancing mineral deposition, and thus are useful in multiple disorders, for example disorders involving either insufficient mineral density in bone (e.g., osteoporosis, osteomalacia, rickets); insufficient bone generation (e.g., osteogenesis imperfecta); and bone erosion.

Thus, one object of the invention is to provide an agent that decreases ANK expression and/or activity to increase mineral deposition in a subject in need thereof.

Agents that increase ANK activity can be useful in decreasing mineral deposition in joints and other tissues, and thus are useful in disorders such as osteoarthritis, calcium pyrophosphate deposition disease, rheumatoid arthritis, undifferentiated spondyloarthropathy and ankylosing spondylitis, calcifying tendonitis, Milwaukee shoulder syndrome, arteriosclerosis, soft tissue calcification, and renal lithiasis.

Thus, another object of the invention is to provide an agent that increases ANK expression and/or activity to decrease mineral deposition in a subject in need thereof.

Another object of the invention is the identification of mutations in the ank gene in a mammalian subject as a diagnostic and/or prognostic indicator, e.g., an indicator of inherited arthritic disorders.

Yet another object of the invention is to provide an assay to identify compounds that modulate ANK expression and/or function. Such compounds may be used as therapeutics for reduction or increase of ANK function, as desired for a particular condition.

Another object of the invention is to provide an isolated human ANK-encoding polynucleotide for use in generation of non-human transgenic animal models for ank gene function, particularly "knock-in" ank non-human transgenic animals characterized by excess or ectopic expression of the ank gene. The knock-in may be in a wild-type background, or may be in a background having a genetic mutation, e.g., a mouse model for osteopenia. The human ank polynucleotide may contain naturally occurring polymorphisms and/or mutations identified that are associated with a disease state, e.g., inherited or spontaneous OA.

These and other objects, advantages, and features of the present invention will become apparent to those persons skilled in the art upon reading the details of the invention more fully set forth below.

The invention will now be described in further detail.

DETAILED DESCRIPTION OF THE INVENTION

Before the present nucleotide and polypeptide sequences are described, it is to be understood that this invention is not limited to the particular methodology, protocols, cell lines, vectors, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a host cell" includes a plurality of such host cells and reference to "the antibody" includes reference to one or more antibodies and equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices, and materials are now described.

All publications mentioned herein are incorporated herein by reference for the purpose of describing and disclosing, for example, the cell lines, vectors, and methodologies which are described in the publications which might be used in connection with the presently described invention. The publications discussed herein are provided solely for their disclosure prior to the filing date of the present application. Nothing herein is to be construed as an admission that the inventors are not entitled to antedate such disclosure by virtue of prior invention.

Definitions "Polynucleotide" as used herein refers to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Where "polynucleotide" is used to refer to a specific polynucleotide sequence (e.g. an ANK-encoding polynucleotide), "polynucleotide" is meant to encompass polynucleotides that encode a polypeptide that is functionally equivalent to the recited polypeptide, e.g. polynucleotides that are degenerate variants, or polynucleotides that encode biologically active variants or fragments of the recited polypeptide.

Similarly, "polypeptide" and "protein" (as in ANK) as used herein refer to an oligopeptide, peptide, or protein. Where "polypeptide" and "protein" are recited herein to refer to an amino acid sequence of a naturally-occurring protein molecule, "polypeptide" and "protein" and like terms are not meant to limit the amino acid sequence to the complete, native amino acid sequence associated with the recited protein molecule.

As used herein "ANK polynucleotide" and "ANK polypeptide" encompass polynucleotides and polypeptides having sequence similarity or sequence identity to the human ANK of the invention of at least about 65%, preferably at least about 80%, more preferably at least about 85%, and can be greater than at least about 90% or more. Sequence similarity and sequence identity are calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. In general, percent sequence identity is calculated by counting the number of residue matches (e.g., nucleotide residue or amino acid residue) between the query and test sequence and dividing total number of matches by the number of residues of the individual sequences found in the region of strongest alignment. Thus, where 10 residues of an 11 residue query sequence matches a test sequence, the percent identity above would be 10 divided by 11, or approximately, 90.9%. Algorithms for computer-based sequence analysis are known in the art, such as BLAST (see, e.g., Altschul et al., *J. Mol. Biol.*, 215:403–10 (1990)), particularly the Smith-Waterman homology search algorithm as implemented in MPSRCH program (Oxford Molecular). For the purposes of this invention, a preferred method of calculating percent identity is the Smith-Waterman algorithm, using the following Global DNA sequence identity must be greater than 65% as determined by the Smith-Waterman homology search algorithm as implemented in MPSRCH program (Oxford Molecular) using an affine gap search with the following search parameters: gap open penalty, 12; and gap extension penalty, 1.

Nucleic acids having sequence similarity can also be detected by hybridization under low stringency conditions, for example, at 50° C. and 6XSSC (0.9 M saline/0.09 M sodium citrate) and remain bound when subjected to washing at 55° C. in 1XSSC (0.15 M sodium chloride/0.015 M sodium citrate). Sequence identity may be determined by hybridization under high stringency conditions, for example, at 50° C. or higher and 0.1×SSC (15 mM saline/1.5 mM sodium citrate). By using probes, particularly labeled probes of DNA sequences, one can isolate homologous or related genes. The source of homologous genes may be any species, e.g. primate species (particularly human), rodents (such as rats and mice), canines, felines, bovines, ovines, equines, yeast, *Drosophila, Caenhorabditis*, etc.

"Antisense polynucleotide" or "antisense oligonucleotide" are used interchangeably herein to mean an unmodified or modified nucleic acid having a nucleotide sequence complementary to a given polynucleotide sequence (e.g., a polynucleotide sequence encoding ANK) including polynucleotide sequences associated with the transcription or translation of the given polynucleotide sequence (e.g., a promoter of a polynucleotide encoding ANK), where the antisense polynucleotide is capable of hybridizing to an ANK-encoding polynucleotide sequence. Of particular interest are antisense polynucleotides capable of inhibiting transcription and/or translation of an ANK-encoding polynucleotide either in vitro or in vivo.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen et al., *Anticancer Drug Des.*, 8:53–63 (1993)).

As used herein "ANK" refers to an amino acid sequence of a recombinant or nonrecombinant polypeptide having an amino acid sequence of i) a native human ANK, ii) a biologically active fragment of ANK, iii) biologically active polypeptide analogs of ANK, or iv) a biologically active variant of ANK. ANK can be obtained from any species, e.g., mammalian or non-mammalian (e.g., reptiles, amphibians, avian (e.g., chicken)), particularly mammalian, including human, rodent (e.g., mouse or rat), bovine, ovine, porcine, or equine, preferably human, from any source whether natural, synthetic, semi-synthetic or recombinant. "Human ANK" refers to the amino acid sequences of isolated human ANK obtained from a human, and is meant to include all naturally-occurring allelic variants, and is not meant to limit the amino acid sequence to the complete, native amino acid sequence associated with the recited protein molecule.

The term "ank gene" is used generically to designate ank genes and their alternate forms. "ank gene" is also intended to mean the open reading frame encoding ANK, introns, and adjacent 5' and 3' non-coding nucleotide sequences involved in the regulation of expression, up to about 1 kb beyond the coding region, but possibly further in either direction. The DNA sequences encoding ANK may be cDNA or genomic DNA or a fragment thereof. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons (e.g., sequences encoding open reading frames of the encoded polypeptide) and 3' and 5' non-coding regions. Normally mRNA species have contiguous exons, with the intervening introns removed by nuclear RNA splicing to create a continuous open reading frame encoding ANK.

As used herein, "antigenic amino acid sequence" means an amino acid sequence that, either alone or in association with a carrier molecule, can elicit an antibody response in a mammal.

A "variant" of a human ANK is defined as an amino acid sequence that is altered by one or more amino acids. The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include amino acid deletions or insertions, or both. Guidance in determining which and how many amino acid residues may be substituted, inserted, or deleted without abolishing biological or immunological activity can be found using computer programs well known in the art, for example, DNAStar software.

A "deletion" is defined as a change in either amino acid or nucleotide sequence in which one or more amino acid or nucleotide residues, respectively, are absent as compared to an amino acid sequence or nucleotide sequence of a naturally occurring ANK.

An "insertion" or "addition" is that change in an amino acid or nucleotide sequence which has resulted in the addition of one or more amino acid or nucleotide residues, respectively, as compared to an amino acid sequence or nucleotide sequence of a naturally occurring ANK.

A "substitution" results from the replacement of one or more amino acids or nucleotides by different amino acids or nucleotides, respectively, as compared to an amino acid sequence or nucleotide sequence of a naturally occurring ANK.

The terms "single nucleotide polymorphism" and "SNP" refer to polymorphisms of a single base change relative to a reference sequence, e.g., the cDNA sequence of SEQ ID NO:1 or the intronic sequences of SED ID NOS:3–14.

The term "biologically active" refers to human ANK having structural, regulatory, or biochemical functions of a naturally occurring ANK. Likewise, "immunologically active" defines the capability of the natural, recombinant, or synthetic human ANK, or any oligopeptide thereof, to induce a specific immune response in appropriate animals or cells and to bind with specific antibodies.

The term "derivative" as used herein refers to the chemical modification of a nucleic acid encoding a human ANK or the encoded human ANK Illustrative of such modifications would be replacement of hydrogen by an alkyl, acyl, or amino group. A nucleic acid derivative would encode a polypeptide which retains essential biological characteristics of a natural ANK.

As used herein the term "isolated" is meant to describe a compound of interest (e.g., either a polynucleotide or a polypeptide) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound (e.g., either a polynucleotide or a polypeptide) that is removed from its natural environment and is at least 60% free, preferably 75% free, and most preferably 90% free from other components with which it is naturally associated.

"Stringency" typically occurs in a range from about Tm-5° C. (5° C. below the Tm of the probe or anti body) to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs, Dictionary of Biotechnology, Stockton Press, New York N.Y. (1994)). Amplification as carried out in the polymerase chain reaction technologies is described in Dieffenbach et al., PCR Primer, a Laboratory Manual, Cold Spring Harbor Press, Plainview N.Y. (1995).

The term "transformation" as used herein refers to a permanent or transient genetic change, preferably a permanent genetic change, induced in a cell following incorporation of new DNA (i.e. DNA exogenous to the cell). Genetic change can be accomplished either by incorporation of the new DNA into the genome of the host cell, or by transient or stable maintenance of the new DNA as an episomal element. Where the cell is a mammalian cell, a permanent genetic change is generally achieved by introduction of the DNA into the genome of the cell.

The term "construct" as used herein refers to a recombinant nucleic acid, generally recombinant DNA, that has been generated for the purpose of the expression of a specific nucleotide sequence(s), or is to be used in the construction of other recombinant nucleotide sequences.

The term "mimetic agent" as used herein describes any molecule, e.g., protein or pharmaceutical, with the capability of altering or mimicking the expression or physiological function of ANK. Generally a plurality of assay mixtures are run in parallel with different agent concentrations to obtain a differential response to the various concentrations. Typically, one of these concentrations serves as a negative control, i.e. at zero concentration or below the level of detection.

The term "operably linked" as used herein refers to a DNA sequence and a regulatory sequence(s) that are connected in such a way as to permit gene expression when the appropriate molecules (e.g., transcriptional activator proteins) are bound to the regulatory sequence(s).

The term "operatively inserted" as used herein refers to a nucleotide sequence of interest that is positioned adjacent a nucleotide sequence that directs transcription and translation of the introduced nucleotide sequence of interest (i.e., facilitates the production of, e.g., a polypeptide encoded by an ANK sequence).

The terms "ANK disorder" and "ANK-associated disorder" as used herein refer to a physiological condition or disease that results from or exhibits a symptom caused by altered ANK function (e.g., due to aberrant ANK expression or a defect in ANK expression or in the ANK protein). Such ANK associated disorders can include disorders associated with either increased or decreased ANK expression.

The term "subject" or "patient" as used herein refers to any mammalian subject for whom diagnosis or therapy is desired, particularly humans.

The term "treatment" is used herein to encompass any treatment of any disease or condition in a mammal, particularly a human, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms. "Condition" or "disease" are used herein to mean any undesirable, abnormal, or pathological state, including those subsequent to accidental or surgical injury (e.g., as in wound healing).

The term "transgene" is used herein to describe genetic material which has been or is about to be artificially inserted into the genome of a mammalian, particularly a mammalian cell of a living animal.

The terms "transgenic organism" and "transgenic animal" as used herein refer to a non-human organism (e.g., single-cell organisms (e.g., yeast), mammal, non-mammal (e.g. nematode or *Drosophila*)) having a non-endogenous (i.e. heterologous) nucleic acid sequence present as an extrachromosomal element in a portion of its cells or stably integrated into its germ line DNA (i.e., in the genomic sequence of most or all of its cells). Heterologous nucleic acid is preferably introduced into the germ line of such transgenic animals by genetic manipulation of, for example, embryos or embryonic stem cells of the host animal.

A "knock-out" of a target gene means an alteration in the sequence of the gene that results in a decrease of function of the target gene, preferably such that target gene expression is undetectable or insignificant. A knock-out of an ank gene means that function of the ank gene has been substantially decreased so that ANK expression is not detectable or only present at insignificant levels. "Knock-out" transgenics of the invention can be transgenic animals having a heterozygous knock-out of the ank gene or a homozygous knock-out of the ank gene. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other methods for directing the target gene alteration postnatally. A "knock-in" of a target gene means an alteration in a host cell genome that results in altered expression (e.g., increased (including ectopic) or decreased expression) of the target gene, e.g., by introduction of an additional copy of the target gene, or by operatively inserting a regulatory sequence that provides for enhanced expression of an endogenous copy of the target gene. "Knock-in" transgenics of the invention can be transgenic animals having a heterozygous knock-in of the ank gene or a homozygous knock-in of the ank gene. "Knock-ins" also encompass conditional knock-ins.

By "antibody" is meant an immunoglobulin protein which is capable of binding an antigen. Antibody as used herein is meant to include the entire antibody as well as any antibody fragments (e.g., $F(ab')_2$, Fab', Fab, Fv) capable of binding the epitope, antigen, or antigenic fragment of interest.

Antibodies of the invention are immunoreactive or immunospecific for and therefore specifically and selectively bind to an ANK protein. Antibodies which are immunoreactive and immunospecific for human ANK are preferred. Antibodies for human ANK are preferably immunospecific—i.e., not substantially cross-reactive with related materials, although they may recognize ANK homologs across species. The term "antibody" encompasses all types of antibodies (e.g., monoclonal and polyclonal).

By "purified antibody" is meant one which is sufficiently free of other proteins, carbohydrates, and lipids with which it is naturally associated. Such an antibody "preferentially binds" to an ANK protein (or an antigenic fragment thereof), i.e., does not substantially recognize and bind to other antigenically-unrelated molecules.

By "antigenic fragment" of an ANK protein is meant a portion of such an ANK protein which is capable of binding an antibody of the invention. Preferably, the antibodies which specifically bind an epitope of the isolated antigenic fragment will also bind the same epitope in the context of the native protein from which the fragment was derived.

By "binds specifically" is meant high avidity and/or high affinity binding of an antibody to a specific polypeptide i.e. epitope of an ANK protein. Antibody binding to its epitope on this specific polypeptide is stronger than binding of the same antibody to any other epitope, particularly those which may be present in molecules in association with, or in the same sample, as the specific polypeptide of interest. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls.

Summary of the Sequence Listing

The polynucleotide and amino acid sequence of human ANK are provided as SEQ ID NOS:1 and 2.

The exon/intron splice junctions of the human ank are provided as SEQ ID NOS:3–14

The polynucleotide and amino acid sequence of murine ANK are provided as SEQ ID NOS:15 and 16.

The oligonucleotide primers used to clone the ank genes and/or amplify different regions of the human ANK gene are provided as SEQ ID NOS:17–102.

Overview of the Invention

The present invention is based upon the identification and isolation of a polynucleotide sequence encoding a novel human protein (ANK). Accordingly, the present invention encompasses such human ANK-encoding polynucleotides, as well as human ANK encoded by such polynucleotides.

ANK, ANK-encoding polynucleotides, or fragments of ANK and/or ANK-encoding polynucleotides can be used as therapeutic agents, or can be used in screening assays to identify agents that alter or replace in vivo human ANK activity. For example, antisense polynucleotides of the ank gene and/or ribozymes based upon the ank gene sequence can be used to inhibit expression of ANK in the treatment of diseases involving an excess of ANK activity. Appropriate antisense polynucleotides and ribozymes can be identified by screening in, for example, in vitro assays for inhibition of ANK expression. In addition to antisense polynucleotides and ribozymes, in vitro and/or in vivo assays can also be used to identify other candidate agents (e.g. small molecules) that modulate ANK activity by, for example, binding to ANK directly, inhibiting ANK expression, or modulating ANK protein interactions.

In addition, the human ANK and polynucleotides of the invention are useful in the diagnosis, prevention, and treatment of disease associated with human ANK biological activity. The invention also encompasses the use of the polynucleotides disclosed herein to facilitate identification and isolation of polynucleotide and polypeptide sequences having homology to a human ANK of the invention. The human ANK-encoding polynucleotides of the invention can also be used as molecular probes with which to determine the structure, location, and expression of the human ANK and related polypeptides in mammals (including humans), and to investigate potential associations between disease states or clinical disorders and defects or alterations in human ANK structure, expression, or function.

Identification of the ank gene will provide a molecular entry point into the study of genes that are important for the proper maintenance of joint morphology and mineralization, and their roles in the etiology of destructive joint diseases like arthritis in humans. The broad tissue distribution of the ank transcript as well as the phenotypes observed in ank mutants outside of joints, e.g., in the kidney, suggest that the ANK gene product may also play an important role in regulating mineral deposition in other skeletal and soft tissues. Identification of this gene mail thus provide a useful target for increasing or decreasing mineral deposition in many other diseases, including osteoporosis, osteoarthritis, calcifying tendonitis, arteriosclerosis, tumor calcification, and renal lithiasis (Fleisch and Bisaz, *Experientia*, 20:276–7 (1964); Anderson, H. C., *Arch. Pathol. Lab. Med.*, 107: 341–8 (1983)).

ANK Nucleic Acid

A genomic sequence of interest comprises the nucleic acid present between the initiation codon and the stop codon including all of the introns that are normally present in a native chromosome. The sequence may further include the 3' and 5' untranslated regions found in the mature mRNA, and specific transcriptional and translational regulatory sequences, such as promoters, enhancers, etc., including about 1 kb, but possibly more, of flanking genomic DNA at either the 5' or 3' end of the transcribed region. A 180 kb segment of genomic DNA containing the ank gene rescues the ankylotic phenotype in ank/ank mutant mice and must contain the DNA sequences sufficient for functional expression of ANK in joints.

The sequence of this 5' region, and further 5' upstream sequences and 3' downstream sequences, may be utilized for promoter elements, including enhancer binding sites, that provide for expression in tissues where ANK is expressed. The sequences of the ank promoter elements of the invention can be based on the nucleotide sequences of any species (e.g., mammalian or non-mammalian (e.g., reptiles, amphibians, avian (e.g. chicken)), particularly mammalian, including human, rodent (e.g., murine or rat), bovine, ovine, porcine, or equine, preferably rat or human) and can be isolated or produced from any source whether natural, synthetic, semi-synthetic, or recombinant.

ank polynucleotides are useful for determining the pattern of ANK expression. Furthermore, ank promoter sequences are useful for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al., *Mol. Med.*, 1: 194–205 (1995); Mortlock et al., *Genome Res.*, 6: 327–33 (1996); and Joulin and Richard-Foy, *Eur. J. Biochem.* 232: 620–626 (1995).

In one embodiment, the ank promoter and its regulatory elements are used to direct expression of genes. The ank promoter can be exploited to facilitate expression of heterologous genes operably linked to the ank promoter. Exemplary genes of interest that can be expressed from the ank promoter include, but are not necessarily limited to, enzynmes that modify cartilage and extracellular matrix components, growth factors, marker genes (e.g., for marking the precursor cells for selection and/or tracing), reporter genes (e.g., luciferase, CAT, etc., for identifying mechanisms for regulating the ank promoter and/or to search for bioactive agents (e.g., candidate pharmaceutical agents) that regulate the promoter), and the like.

The regulatory sequences may be used to identify cis acting sequences required for transcriptional or translational regulation of ANK expression (e.g., in different tissues, different stages of development, or in different disease states) and to identify cis acting sequences and trans acting factors that regulate or mediate ANK expression. Such transcriptional or translational control regions may be operably linked to an ank gene or other genes in order to promote expression of wild type or altered ANK or other proteins of interest in cultured cells, or in embryonic, fetal, or adult tissues, and for gene therapy. ANK transcriptional or translational control regions can also be used to identify extracellular signal molecules that regulate ank promoter activity, and thus regulate ANK expression and mineral deposition in joints and other tissues.

The nucleic acid compositions used in the subject invention may encode all or a part of ANK as appropriate. Fragments may be obtained of the DNA sequence by chemically synthesizing oligonucleotides in accordance with conventional methods, by restriction enzyme digestion, by PCR amplification, etc. For the most part, DNA fragments will be of at least about ten contiguous nucleotides (nt), usually at least about 15 nt, more usually at least about 18 nt to about 20 nt, more usually at least about 25 nt to about 50 nt. Such small DNA fragments are useful as primers for PCR, hybridization screening, etc. Larger DNA fragments, i.e. greater than 100 nt, are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

ank polynucleotides, including the ank gene, are isolated and obtained in substantial purity, generally as other than an intact mammalian chromosome. Usually, the DNA will be obtained substantially free of other nucleic acid sequences that do not include an ank sequence or fragment thereof, generally being at least about 50%, usually at least about 90%, pure and is typically "recombinant", i.e. flanked by one or more nucleotides with which it is not normally associated on a naturally occurring chromosome.

The DNA sequences are used in a variety of ways. They may be used as probes for identifying homologs of ANK. Mammalian homologs have substantial sequence similarity to one another, i.e. at least 75%, usually at least 90%, more usually at least 95% sequence similarity. The ANK-encoding DNA may also be used to identify expression of the gene in a biological specimen. The manner in which one probes cells for the presence of particular nucleotide sequences, as genomic DNA or RNA, is well established in the literature and does not require elaboration here. mRNA is isolated from a cell sample. mRNA may be amplified by RT-PCR, using reverse transcriptase to form a complementary DNA strand, followed by polymerase chain reaction amplification using primers specific for the subject DNA sequences. Alternatively, mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to an ANK sequence is indicative of ank gene expression in the sample.

The ank nucleic acid sequence may be modified for a number of purposes, particularly where it will be used intracellularly, for example, by being joined to a nucleic acid cleaving agent, e.g., a chelated metal ion such as iron or chromium, for cleavage of the gene; or the like.

The sequence of the ank locus, including flaring promoter regions and coding regions, may be mutated in various ways known in the art to generate targeted changes in promoter strength, sequence of the encoded protein, etc. The DNA sequence or product of such a mutation will be substantially similar to the sequences provided herein, i.e. will differ by at least one nucleotide or amino acid, respectively, and may differ by at least two but not more than about ten nucleotides or amino acids. The sequence changes may be substitutions, insertions, or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used. Such mutated genes may be used to study structure-function relationships of ANK with other polypeptides, or to alter properties of the proteins that affect their function or regulation. Such modified ANK sequences can be used, for example, to generate transgenic animals.

Techniques for in vitro mutagenesis of cloned genes are known. Examples of protocols for scanning mutations may be found in Gustin et al., *Biotechniques*, 14:22 (1993); Barany, *Gene*, 37:111–23 (1985); Colicelli et al., *Mol. Gen. Genet.*, 199:537–9 (1985); and Prentki et al., *Gene* 29:303–13 (1984). Methods for site specific mutagenesis can be found in Sambrook et al., Molecular Cloning: A Laboratory Manual, CSH Press, pp. 15.3–15.108 (1989); Weiner et al., *Gene*, 126:35–41 (1993); Sayers et al., *Biotechniques*, 13:592–6 (1992); Jones and Winistorfer, *Biotechniques*, 12:528–30 (1992); Barton et al., *Nucleic Acids Res.*, 18:7349–55 (1990): Marotti and Tomich, *Gene. Anal Tech.*, 6:67–70 (1989); and Zhu, *Anal. Biochem.*, 177:120–4 (1989).

Antisense Oligonucleotides

The invention also encompasses antisense oligonucleotides that modulate ANK expression in vivo. In general, "oligonucleotide" (which is used interchangeably herein with polynucleotide) represents an oligonucleotide made up of bases (either ribonucleic acid, deoxyribonucleic acid, or both), phosphodiester bonds and sugars as well known by persons skilled in the art. The oligonucleotides of the invention encompass unmodified as well modified oligonucleotides, e.g., oligonucleotides in which the skeleton has been modified either on the entire length of the oligonucleotide or in the 5' position and/or in the 3' position.

The oligonucleotides of the invention may be synthesized by recombinant methods, or by any of the known methods of chemical synthesis of oligonucleotides. For example, antisense oligonucleotides can be prepared using any automatic synthesizer of commercial nucleic acids. An exemplary method of oligonucleotide synthesis is the beta-cyanoethyl phosphoramidate method described by Beaucage et al., *Tet. Let.*, 22:1859–1862 (1981).

In most instances it is generally desirable to provide the oligonucleotide as a modified oligonucleotide. Oligonucleotides, which are generally sensitive to nucleases, can be rendered resistant to nucleases by modifications, for example, from the chemical nature of sugar itself or the sugar-phosphate chain. In this manner the phosphodiester chain may be replaced, for example, by a phosphorothioate, phosphorodithioate, methylphosphonate, phosphoramidate, phosphoethlytriester, butylamidate, piperazidate, or morpholidate chains. Other types of modifications may be made along the entire length of the oligonucleotide or to its 5' and/or 3' extremities, to render the oligonucleotides more resistant to a biological environment. Phosphate bonds between the nucleotides may also be replaced by amide bonds (peptidic nucleic acids). Moreover, the transmembranous passage of the oligonucleotide may be favored by rendering the latter more hydrophobic; this may be obtained, for example, by attaching hydrophobic substituents such as cholesterol or aromatic groups or a polymer. The modified bases may be partially incorporated or along the entire length of the oligonucleotide. Conformationally modified nucleotides resistant to nucleases or with improved properties of intracellular absorption or hybridization may be incorporated partially or along the entire length of the nucleotide. Methods and compositions for generating modified oligonucleotides are well known in the art.

In general, antisense oligonucleotides are from about 15 nucleotides (nt) to about 100 nt, normally from about 17 nt to about 75 nt, usually from about 20 nt to about 50 nt in length, more usually about 30 nt to about 40 nt, and normally about 40 nt in length. A contemplated polynucleotide hybridizes to about 10 nt to about 25 nt, more preferably about 15 nt to about 20 nt, and most preferably about 20 nt flanking the start codon of the mRNA that encodes ANK or to a region of the ank promoter. Based on an estimated size of approximately $3 \times 10^9$ base pairs for the human genome, a sequence of 17 nt should occur only once. For specific exemplary antisense oligonucleotides, as well as methods and compositions for the design, manufacture, and delivery of oligonucleotides as therapeutics, see, e.g., U.S. Pat. Nos. 5,892,023; 5,891,858; 5,891,725; and 5,885,834.

Ribozymes

Ribozymes are trans-cleaving catalytic RNAs that exhibit endoribonuclease activity in a sequence-specific manner. The cleavage event facilitated by ribozymes renders the target mRNA unstable and prevents protein expression. The hammerhead motif is one commonly used ribozyme motif having minimal substrate requirements. Design of the hammerhead ribozyme, as well as its therapeutic uses, is disclosed in, e.g., Usman et al., *Current Opin. Struct. Biol.*, 6:527 (1996); Long et al., *FASEB J.*, 7:25 (1993); Symons, *Ann. Rev. Biochem.*, 61:641 (1992); Perrotta et al., *Biochem.*, 31:16 (1992); Ojwang et al., *Proc. Natl. Acad. Sci. (USA)*, 89:10802 (1992); Koizumi et al., *Nucleic Acid Res.*, 17:7059 (1989); and in U.S. Pat. Nos. 5,254,678; 5,116,742; and 5,225,337.

Alternatively, ribozymes can be made in a hairpin structure (see, e.g., Chowrira et al., *Nucleic Acids Res.*, 20:2835 (1992)), by rolling transcription (see, e.g., Daubendiek et al., *Nat. Biotechnol.*, 15(3):273 (1997)), or as a branched structure (see, e.g., Horn et al., *Nucleic Acids Res.*, 17:6959 (1989)). The basic structure of the ribozymes can also be chemically altered in ways familiar to those skilled in the art, and chemically synthesized ribozymes can be administered as synthetic oligonucleotide derivatives modified by monomeric units.

Using the polynucleotide sequences of the invention and methods known in the art, ribozymes are designed to specifically bind, cut, and thus render substantially nonfunctional ANK-encoding mRNA. Ribozymes thus provide a means to inhibit the expression of any of the proteins encoded by the disclosed polynucleotides or their full-length genes. Ribozymes corresponding to the ank gene can be tested in vitro for efficacy in cleaving the target transcript, and the activity of those ribozymes that effect cleavage in vitro further tested in vivo.

In general, ribozymes are constructed by first selecting a target cleavage site in the target ank gene, and constructing a ribozyme based on the 5' and 3' nucleotide sequences that flank the cleavage site. Retroviral vectors are engineered to express monomeric and multimeric hammerhead ribozymes targeting the mRNA of the target coding sequence. These monomeric and multimeric ribozymes are tested in vitro for an ability to cleave the target mRNA. A cell line is stably transduced with the retroviral vectors expressing the ribozymes, and the transduction is confirmed by Northern blot analysis and reverse-transcription polymerase chain reaction (RT-PCR). The cells are screened for inactivation of the target mRNA by such indicators as reduction of expression of disease markers or reduction of the gene product of the target mRNA.

Production of ANK

ANK-encoding nucleic acid may be employed to synthesize full-length ANK or fragments thereof, particularly fragments corresponding to functional domains; DNA binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, or cells of a higher organism such as vertebrates, particularly mammals, e.g. COS 7 cells, may be used as the expression host cells. In many situations, it may be desirable to express the ANK genes in mammalian cells, especially where the encoded polypeptides will benefit from native folding and post-translational modifications. Small peptides can also be synthesized in the laboratory.

With the availability of the polypeptides in large amounts, by employing an expression host, the polypeptides may be isolated and purified in accordance with conventional ways. A lysate may be prepared of the expression host and the lysate purified using HPLC, exclusion chromatography, gel electrophoresis, affinity chromatography, or other purification techniques. The purified polypeptide will generally be at least about 80% pure, preferably at least about 90% pure, and may be up to and including 100% pure. Pure is intended to mean free of other proteins, as well as cellular debris.

The ANK protein can be used for the production of antibodies, where short fragments provide for antibodies specific for the particular polypeptide, and larger fragments or the entire protein allow for the production of antibodies over the surface of the polypeptide. Antibodies may be raised to the wild-type or mutant forms of ANK. Antibodies may be raised to isolated peptides corresponding to these domains, or to the native protein, e.g. by immunization with cells expressing ANK, immunization with liposomes having ANK inserted in the membrane, etc.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by, cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

Isolation of ank Allelic Variants and Homologues in Other Species

Other mammalian ank genes can be identified and their function characterized using the ank genes used in the present invention. Other ank genes of interest include, but are not limited to, mammalian (e.g., human, rodent (e.g., rat), bovine, feline, canine, and the like) and non-mammalian (e.g., chicken, reptile, shark, and the like). Methods for identifying, isolating, sequencing, and characterizing an unknown gene based upon its homology to a known gene sequence are well known in the art (see, e.g., Sambrook et al., Molecular Cloning: A Laboratory Manual, CSH Press 1989).

Drug Screening Assays

The animal models of the invention, as well as methods using the ANK protein in vitro, can be used to identify candidate agents that affect ANK expression (e.g., by affecting ank promoter function) or that otherwise affect ANK activity. Agents of interest include those that enhance, inhibit, regulate, replace, or otherwise affect activity and/or expression. Of particular interest in the present invention is the identification of synthetic molecules that have activity in either enhancing or inhibiting ANK activity. Assay screening can be designed to identify synthetic molecules that act to either enhance or inhibit ANK expression and/or activity. Of particular interest are screening assays for agents that have a low toxicity for human cells. Agents that alter ANK activity and/or expression can be used to, for example, treat or study disorders associated with decreased ANK activity. "Candidate agents" is meant to include synthetic molecules (e.g., small molecule drugs, peptides, or other synthetically produced molecules or compounds, as well as recombinantly produced gene products) as well as naturally-occurring compounds (e.g., polypeptides, endogenous factors present in mammalian cells, hormones, plant extracts, and the like).

Candidate mimetic and/or therapeutic agents encompass numerous chemical classes, including, but not limited to, antisense polynucleotides, ribozymes, and organic molecules, e.g., small organic compounds having a molecular weight of more than 50 and less than about 2,500 daltons. Candidate agents can comprise functional groups necessary for structural interaction with proteins, particularly hydrogen bonding, and typically include at least an amine, carbonyl, hydroxyl, or carboxyl group, preferably at least two of the functional chemical groups. The candidate agents often comprise cyclical carbon or heterocyclic structures and/or aromatic or poly aromatic structures substituted with one or more of the above functional groups. Candidate agents are also found among biomolecules including, but not limited to: polynucleotides, peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant, and animal extracts are available or readily produced. Additionally, natural or synthetically produced libraries and compounds are readily modified through conventional chemical, physical, and biochemical means, and may be used to produce combinatorial libraries. Known pharmacological agents may be subjected to directed or random chemical modifications, such as acylation, alkylation, esterification, amidification, etc. to produce structural analogs.

Agents that inhibit ANK activity, e.g., by inhibiting ANK expression or activity, are of interest as enhancers of mineral deposition in joints and other soft tissues. Such agents can be the basis for, for example, therapeutic agents (drugs) for the treatment of conditions associated with abnormally low mineral deposition. Examples of conditions that can benefit from treatment with such inhibitors of ANK activity include, but are not necessarily limited to, disorders involving either insufficient mineral density in bone (such as osteoporosis, osteomalacia, rickets), disorders with insufficient bone generation (such as osteogenesis imperfecta), and bone erosion.

Agents that promote ANK activity (i.e., increase ANK activity by, for example, promoting ANK binding to other proteins, by increasing ANK expression, and the like) are of interest as inhibitors of excessive joint and soft tissue mineralization. Examples of conditions that can benefit from agents that promote ANK activity, such as ANK mimetic agents, include, but are not necessarily limited to, osteoarthritis, calcium pyrophosphate deposition disease, rheumatoid arthritis, undifferentiated spondyloarthropathy and ankylosing spondylitis, calcifying tendonitis, renal lithiasis, Paget's disease, Milwaukee shoulder syndrome, arteriosclerosis, calcification of blood vessels and other soft tissues, and the like.

Screening of Candidate Agents In Vivo

Agents can be screened for their ability to affect ANK activity or to mitigate an undesirable phenotype (e.g., a symptom) associated with an ANK-associated disease, e.g. OA. The candidate agents can be screened in either transgenic animals expressing human ANK, in animals that are transgenic for an alteration in human ank, or preferably in a transgenic animal with an altered, endogenous ank gene that expresses a normal, polymorphic or mutated form of human ank.

In general, the candidate agent is administered to a non-human transgenic animal, and the effects of the candidate agent determined. The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired affect is to be achieved), orally, or by any other desirable means, and preferably is administered intercerebrally. Normally, the in vivo screen will involve a number of animals receiving varying amounts and concentrations of the candidate agent (from no agent to an amount of agent that approaches an upper limit of the amount that can be delivered successfully to the animal), and may include delivery of the agent in different formulations. The agents can be administered singly or in combinations of two or more, especially where administration of a combination of agents may result in a synergistic effect.

The effect of agent administration upon the transgenic animal can be monitored by assessing ANK function as appropriate (e.g., by examining expression of a reporter or fusion gene), or by assessing a phenotype associated with ANK expression (e.g., by examining joint flexibility, tissue histology, or levels of intracellular or extracellular pyrophosphate). Methods for assaying levels of a selected polypeptide, levels of enzymatic activity, and the like are well known in the art.

Where the in vivo screening assay is to identify agents that affect the activity of the ank promoter and the non-human transgenic animal (or cultured mammalian cell line) comprises an ank promoter operably linked to a reporter gene, the effects of candidate agents upon ank promoter activity can be screened by, for example, monitoring the expression from the ank promoter (through detection of the reporter gene) and correlation of altered ank promoter activity with expression. Alternatively or in addition, ank promoter activity can be assessed by detection (qualitative or quantitative) of ank mRNA or protein levels.

In another embodiment, the transgenic animal comprises an altered ank gene comprising a reporter gene. Activity of candidate agents upon ANK activity can be assessed by examining the relative levels of reporter gene production. Where the candidate agent affects ANK expression, and/or affects an ANK-associated phenotype, in a desired manner, the candidate agent is identified as an agent suitable for use in therapy of an ANK-associated-disorder. It should be noted that, in some instances, it may be advantageous to first screen candidate agents in an in vitro assay as described below.

Screening of Candidate Agents In Vitro

A wide variety of in vitro assays may be used to screen candidate agents for the desired biological activity, including, but not limited to, labeled in vitro protein-protein binding assays, protein-DNA binding assays, electrophoretic mobility shift assays, immunoassays for protein binding, and the like. For example, by providing for the production of large amounts of ANK protein, one can identify ligands or substrates that bind to, modulate, or mimic the action of the proteins. The purified protein may also be used for determination of three-dimensional crystal structure, which can be used for modeling intermolecular interactions, transcriptional regulation, etc.

The screening assay can be a binding assay, wherein one or more of the molecules may be joined to a label, and the label directly or indirectly provides a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assays described herein. Where the assay is a binding assay, these include reagents like salts, neutral proteins, e.g. albumin, detergents, etc. that are used to facilitate optimal protein-protein binding, protein-DNA binding, and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hour will be sufficient.

Other assays of interest detect agents that mimic ANK function. For example, candidate agents are added to a cell that lacks functional ANK, and screened for the ability to reproduce ANK activity in a functional assay.

Many mammalian genes have homologs in yeast and lower animals. The study of such homologs' physiological role and interactions with other proteins in vivo or in vitro can facilitate understanding of biological function. In addition to model systems based on genetic complementation, yeast has been shown to be a powerful tool for studying protein-protein interactions through the two hybrid system described in Chien et al., *Proc. Natl. Acad. Sci. USA*, 88:9578–9582 (1991). Two-hybrid system analysis is of particular interest for exploring transcriptional activation by ANK proteins and to identify cDNAs encoding polypeptides that interact with ANK.

Identified Candidate Agents

Compounds having the desired pharmacological activity may be administered in a physiologically acceptable carrier to a host for treatment of a condition that is amenable to treatment by modulation of ANK activity. The compounds may also be used to enhance ANK function. The therapeutic agents may be administered in a variety of ways, orally, topically, parenterally e.g. subcutaneously, intraperitoneally, by viral infection, intravascularly, etc. Inhaled treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions, and the like. Pharmaceutical grade organic or inorganic carriers and/or diluents suitable for oral and topical use can be used to make up compositions containing the therapeutically-active compounds. Diluents known to the art include aqueous media, vegetable and animal oils, and fats. Stabilizing agents, wetting and emulsifying agents, salts for varying the osmotic pressure, or buffers for securing an adequate pH value, and skin penetration enhancers can be used as auxiliary agents.

Detection of Conditions Amenable to ANK-Based Therapy

The ANK-encoding polynucleotides and polypeptides of the invention can also be used to identify subject having a condition amenable to treatment by modulation of ANK activity (e.g., a condition that can be treated by modulating mineral deposition). Diagnosis of such conditions or disorders can be performed by protein, DNA or RNA sequence and/or hybridization analysis of any convenient sample from a patient, e.g. biopsy material, blood sample, scrapings from cheek, etc., to examine levels of ANK expression, ANK activity, etc.

For example, a nucleic acid sample from a patient having a disorder that is amenable to treatment by ANK modulation can be analyzed for the presence of a predisposing polymorphism in ANK. A typical patient genotype will have at least one predisposing mutation on at least one chromosome. The presence of a polymorphic ANK sequence that affects the activity or expression of the gene product and confers an increased susceptibility to an ANK associated disorder is considered a predisposing polymorphism. Individuals are screened by analyzing their DNA or mRNA for the presence of a predisposing polymorphism, as compared to sequence from an unaffected individual(s). Specific sequences of interest include, for example, any polymorphism that is associated with arthritis, especially osteoarthritis, tissue calcification, or other hereditary condition that is susceptible to treatment by ANK modulation, including, but not limited to, insertions, substitutions, and deletions in the coding region sequence, intron sequences that affect splicing, or promoter or enhancer sequences that affect the activity and expression of the protein.

Biochemical studies may be performed to determine whether a candidate sequence polymorphism in the ank coding region or control regions is associated with disease. For example, a change in the promoter or enhancer sequence that affects expression of ANK may result in predisposition to arthritis. Expression levels of a candidate variant allele are compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like. The activity of the encoded ANK protein may be determined by comparison with the wild-type protein.

Screening may also be based on the functional or antigenic characteristics of the protein. Immunoassays designed to detect predisposing polymorphisms in ANK or aberrant ank mRNA or protein levels may be used in screening. Where many diverse mutations lead to a particular disease phenotype, functional protein assays can be effective screening tools.

A number of methods are available for analyzing nucleic acids for the presence of a specific sequence, e.g., to examine a sample for a polymorphism and/or to examine the level of ank mRNA production. Where large amounts of DNA are available for polymorphism analysis, genomic DNA is used directly. Alternatively, the region of interest is cloned into a suitable vector and grown in sufficient quantity for analysis.

Cells that express ank genes may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki et al., *Science*, 239:487 (1985); a review of current techniques may be found in Sambrook et al., *Molecular Cloning: A Laboratory Manual*, CSH Press, pp. 14.2–14.33 (1989). Amplification may also be used to determine whether a polymorphism is present, by using a primer that is specific for the polymorphism or by determining the sequence of the amplified product.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2', 4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}$S, $^3$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Analysis of relative ANK transcriptional levels, ANK polymorphisms, and ANK mutations can also be performed using polynucleotide arrays, and detecting the pattern of hybridization to the array, e.g., both the identity of the sequences on the array to which the sample hybridizes and/or the relative levels of hybridization (e.g., qualitative or quantitative differences in levels of expression). The hybridization pattern of a control and test sample to an array of oligonucleotide probes immobilized on a solid support, as described in U.S. Pat. No. 5,445,934, or in WO95/35505, may be used in such assays. In one embodiment of the invention, an array of oligonucleotides is provided, where discrete positions on the array are complementary to at least a portion of mRNA or genomic DNA of the ank locus. Such an array may comprise a series of oligonucleotides, each of which can specifically hybridize to a nucleic acid sequence, e.g., mRNA, cDNA, genomic DNA, etc. from the ank locus. For detection of ANK polymorphisms, the array will normally include at least 2 different polymorphic sequences, i.e. polymorphisms located at unique positions within the locus, usually at least about 5, more usually at least about 10, and may include as many as 50 to 100 different polymorphisms. The oligonucleotide sequence on the array will usually be at least about 12 nt in length, may be the length of the provided ank sequence, or may extend into the flanking regions to generate fragments of 100 to 200 nt in length. For examples of arrays, see Hacia et al., *Nature Genetics* 14:441–447 (1996); Lockhart et al., *Nature Biotechnol.,* 14:1675–1680 (1996); and De Risi et al., *Nature Genetics,* 14:457–460 (1996).

Antibodies specific for ANK or ANK variants (e.g., ANK proteins with polymorphisms) may be used in screening immunoassays to detect relative levels of ANK or ANK variants. A reduction or increase in ANK and/or presence of an ANK disorder-associated polymorphism is indicative that the suspected disorder is ANK-associated. In general, such screening immunoassays are performed by obtaining a sample from a patient suspected of having an ANK-associated disorder. "Samples," as used herein, include tissue biopsies, biological fluids, organ or tissue culture derived fluids, and fluids extracted from physiological tissues, as well as derivatives and fractions of such fluids. The number of cells in a sample will generally be at least about $10^3$, usually at least $10^4$, more usually at least about $10^5$. The cells may be dissociated, in the case of solid tissues, or tissue sections may be analyzed. Alternatively a lysate of the cells may be prepared.

Diagnosis may be performed by a number of methods. The different methods all determine the absence or presence or altered amounts of normal or abnormal ANK in patient cells. For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and ANK in a lysate. Measuring the concentration of ANK binding in a sample or fraction thereof may be accomplished by a variety of specific assays. A conventional sandwich type assay may be used. For example, a sandwich assay may first attach ANK-specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes, and microtiter plates. These are typically made of glass, plastic (e.g. polystyrene), polysaccharides, nylon, or nitrocellulose. Microtiter plates are especially convenient because a large number of assays can be carried out simultaneously, using small amounts of reagents and samples.

Patient sample lysates are then added to separately assayable supports (for example, separate wells of a microtiter plate) containing antibodies. Preferably, a series of standards, containing known concentrations of ANK (e.g., normal and/or abnormal ANK) are assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, a solution containing a second antibody is applied. The antibody will bind ANK with sufficient specificity such that it can be distinguished from other components present. The second antibodies may be labeled to facilitate direct or indirect quantification of binding. Examples of labels that permit direct measurement of second receptor binding include radiolabels, such as $^3$H or $^{125}$I, fluorescers, dyes, beads, chemiluminescers, colloidal particles, and the like. Examples of labels which permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. When none is commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for ANK as desired, conveniently using a labeling method as described for the sandwich assay.

Other diagnostic assays of interest are based on the functional properties of ANK proteins. Such assays are particularly useful where a large number of different sequence changes lead to a common phenotype. For example, a functional assay may be based on the transcriptional changes mediated by ANK gene products. Other assays may, for example, detect conformational changes, size changes resulting from insertions, deletions or truncations, or changes in the subcellular localization of ANK proteins.

In a protein truncation test, PCR fragments amplified from the ank gene or its transcript are used as templates for in vivo transcription/translation reactions to generate protein products. Separation by gel electrophoresis is performed to determine whether the polymorphic gene encodes a truncated protein, where truncations may be associated with a loss of function.

Identification and Detection of Single Nucleotide Polymorphisms in the ank Gene

In a specific embodiment, the present invention provides single nucleotide polymorphisms (SNPs) in the ank locus, and methods of identifyig and detecting such SNPs. The ank SNPs have utility in a wide variety of methods, including, but not limited to, linkage analysis for the identification of disease loci, evolutionary studies to determine rates of evolution in a population, identification of polymorphisms useful in forensic identification, identification of mutations associated with a disease or predisposition, genetic marker development, and the like. Specific polymorphic sites may be quantified in a selected group (e.g., individuals in families with a history of a bone mineral disorder) or population (e.g., individuals of a certain race or ethnicity) to determine the presence of a particular SNP in that group or population.

In a particular example, ank SNPs of the present invention can be used in screening methods for the evaluation of predispositions for disorders and the use and/or efficacy of therapeutic treatments for the treatment or prevention of such disorders, e.g. arthritis. The presence or absence of a particular allele in an individual can be predictive of the disorder in an individual. Moreover, certain therapeutic agents may be particularly effective for an individual having a particular allele, and so identification of the allele also identifies an individual who is a good candidate for treatment with a particular therapy.

The ank SNPs can also be used for forensic applications such as DNA fingerprinting. DNA fingerprinting requires the identification of a set of polymorphic loci, selected so that the probability that two individual DNA samples with identical haplotypes could by chance come from different individuals is very low.

Preferably, the SNPs of the present invention are identified by analysis of nucleic acid oligomers. The nucleic acid oligomers to be evaluated may be isolated using any number of various techniques available to one skilled in the art. For example, where it is desirable to detect an SNP in a specific region of the ank locus, a DNA sample from an individual may be used as a template for amplification of the region using the polymerase chain reaction (PCR). This method will produce an amplicon that can be tested for the presence of a selected polymorphism. In another example, a sample may be obtained from amplification of a selected region of mRNA, e.g., a region of mRNA that may contain a mutation associated with a disease state. Suitable templates for a PCR reaction to prepare such an amplicon include, but are not limited to, DNA isolated from a subject, RNA isolated from a subject, either total or mRNA, or a cDNA library prepared from cells or tissue of a subject. The reactions themselves can be optimized by those skilled in the art based on variables such as the length of the oligomer to be amplified, the G-C content of the oligomer to be amplified, the template used, and the like. See e.g., *PCR Strategies*, eds. by M. A. Innis, D. H. Gelfand, J. J. Sninsky and J. I. Sninksy both of which are incorporated herein by reference.

In another example, a nucleic acid region of interest can also be isolated using a technique such as reverse transcription of RNA. The RNA used as template for the reverse transcriptase may be preselected (e.g., through oligo-dT selection) or total RNA. Enzymes that may be used in the reverse transcriptase reaction include, but are not limited to, commercially available enzymes such as Avian Myeloblastosis Virus (AMV) Reverse Transcriptase and MoMLV Reverse Transcriptase.

In yet another example, a nucleic acid region of interest may be isolated using a combination and/or modification of reverse transcription and PCR techniques, such as reverse-transcribed PCR (RT-PCR). These and other methods are described in detail in *The PCR Technique: RT-PCR* (The BioTechniques Update Series)—ed. P. D. Siebert (1998), which is incorporated herein by reference.

In yet another example, a nucleic acid region of interest may be isolated by restriction endonuclease digest and purification of a selected oligomer containing an SNP. The DNA is optionally enriched prior to the restriction digest (e.g., purification of a particular region of a chromosome using a technique such as pulse-filed gel electrophoresis). DNA is digested and purified using techniques known in the art (Sambrook et al., Molecular Cloning: A Laboratory Manual Cold Spring Harbor Laboratory Press, Vol. 2 (1989).

The nucleic acid oligomers to be analyzed using the methods of the invention are preferably shorter oligomers, e.g., oligonucleotides ranging from 10 to 200 nucleotides in length, and more preferably oligomers from about 40–90. Thus, although the methods of the invention described herein are described with respect to and optimized for shorter oligonucleotides, the methods can be optimized to distinguish single base polymorphisms in longer oligomers as will be apparent to one skilled in the art upon reading the present specification.

The sample nucleic acid is analyzed by one of a number of methods known in the art. Polymorphism analysis can be performed by sequencing the nucleic acid by dideoxy or other methods, and comparing the sequence to either a neutral ANK sequence (e.g., an ANK sequence from an unaffected individual) or to a known, affected ANK sequence (e.g., an ANK sequence of a known polymorphism). Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size-fractionated to determine whether the fragment was digested. Fractionation is performed by gel or capillary electrophoresis, particularly using acrylamide or agarose gels.

Therapeutic Uses of ANK-Encodining Nucleic Acid

Introduction of the ank nucleic acid (e.g., ANK-encoding polynucleotides, antisense ank polynucleotides, ribozymes, and other ANK-based polynucleotides) into cells can be accomplished according to methods well known in the art (e.g., through use of electroporation, microinjection, lipofection infection with a recombinant (preferably replication-deficient) virus, and other means well known in the art). Preferably, the ank polynucleotide of interest is operably linked to a promoter that facilitates a desired level of expression (e.g., a promoter derived from CMV, SV40, adenovirus, or a tissue-specific or cell type-specific promoter).

ank nucleic acid can be delivered directly to an affected subject to provide for ANK expression in a target cell, thereby promote treatment of a defect in ANK expression in the subject. Methods for in vivo delivery of a nucleic acid of interest for expression in a target cell are known in the art. For example, in vivo methods of gene delivery normally employ either a biological means of introducing the DNA into the target cells (e.g., a virus containing the DNA of interest) or a mechanical means to introduce the DNA into the target cells (e.g., direct injection of DNA into the cells, liposome fusion, pneumatic injection using a "gene gun," etc.).

The amount of DNA and/or the number of infectious viral particles effective to infect the targeted tissue, transform a sufficient number of cells, and provide for production of a desired level of ANK can be readily determined based upon such factors as the efficiency of the transfection in vitro and the susceptibility of the targeted cells to transfection. For example, the amount of DNA injected into a human is, for example, generally from about 1 μg to 750 mg, preferably from about 500 μg to 500 mg, more preferably from about 10 mg to 200 mg, most preferably about 100 mg. Generally, the amounts of DNA can be extrapolated from the amounts of DNA effective for delivery and expression of the desired gene in an animal model. For example, the amount of DNA for delivery in a human is roughly 100 times the amount of DNA effective in a rat.

Ex vivo ank Nucleic Acid Therapy

Where it is desirable to decrease the level of mineral deposition, ANK-encoding nucleic acid can be introduced into a cell to accomplish transfection of the cell, preferably stable transfection, and the transfected cell subsequently implanted into the subject. Preferably, the host cell to be transfected and implanted in the subject is derived from the individual who will receive the transplant (e.g., to provide an autologous transplant).

Transfected cells containing the ank nucleic acid can be selected and/or enriched via, for example, expression of a selectable marker gene present in the ANK-encoding construct or that is present on a plasmid that is co-transfected with the ANK-encoding construct. Typically selectable markers provide for resistance to antibiotics such as tetracycline, hygromycin, neomycin, and the like. Other markers can include thymidine kinase and the like. The ability of the transfected cells to express Other markers can include thymidine kinase and the like. The ability of the transfected cells to express the ank nucleic acid can be assessed by various methods known in the art. For example, ank expression can be examined by Northern blot to detect mRNA which hybridizes with a DNA probe derived from the relevant gene. Those cells that express the desired gene can be further isolated and expanded in in vitro culture using methods well known in the art. The host cells selected for transfection with ank nucleic acid will vary with the purpose of the ex vivo therapy, the site of implantation of the cells, and other factors that will vary with a variety of factors that will be appreciated by the ordinarily skilled artisan.

Methods for engineering a host cell for expression of a desired gene product(s) and implantation or transplantation of the engineered cells (e.g., ex vivo therapy) are known in the art. After expansion of the transfected cells in vitro, the cells are implanted into the mammalian subject, preferably into the tissue from which the cells were originally derived, by methods well known in the art. The number of cells implanted is a number of cells sufficient to provide for expression of levels of ANK sufficient to confer enhanced ANK levels. The number of cells to be transplanted can be determined based upon such factors as the levels of polypeptide expression achieved in vitro, and/or the number of cells that survive implantation. Preferably the cells are implanted in an area of dense vascularization, and in a manner that minimizes evidence of surgery in the subject. The engraftment of the implant of tansfected cells is monitored by examining the mammalian subject for classic signs of graft rejection, i.e., inflammation and/or exfoliation at the site of implantation, and fever.

Regardless of whether the ANK-encoding DNA is introduced in vivo or ex vivo, the DNA (or cells expressing the DNA) can be administered in combination with other genes and other agents. In addition, ANK-encoding DNA (or recombinant cells expressing ANK DNA) can be used therapeutically for disorders associated with, for example, a decrease in ANK production, but which are not associated with an alteration in ANK function per se.

In vivo ANK Nucleic Acid-Based Therapy

ANK nucleic acid-based agents that inhibit or enhance ANK expression, function, or activity, including nucleotides, polypeptides, and other molecules such as antisense oligonucleotides and ribozymes, and dominant negative mutants can be made according to the invention and techniques known to the art. Dominant-negative forms of ANK that effectively displace or compete with native ANK can be used to increase or decrease mineral deposition in joints or other soft tissue. Reagents that inhibit or enhance the expression of endogenous ank genes are also useful.

Nucleotide sequences, including antisense sequences, can be therapeutically administered by various techniques known to those skilled in the art. Delivery of ank nucleotide sequences can be achieved using free polynucleotide or a recombinant expression vector such as a chimeric virus or a colloidal dispersion system. Especially preferred for therapeutic delivery of nucleotide sequences is the use of targeted liposomes.

Targeting of the therapeutic reagent to specific tissues is desirable to increase the efficiency of delivery. The targeting can be achieved by passive mechanisms via the route of administration. Active targeting to specific tissues can also be employed. The use of liposomes, colloidal suspensions, and viral vectors allows targeting to specific tissues by changing the composition of the formulation containing the therapeutic reagent, for example, by including molecules that act as receptors for components of the target tissues. Examples include sugars, glycoplipids, polynucleotides, or proteins. These molecules can be included with the therapeutic reagent. Alternatively, these molecules can be included by indirect methods, for example, by inclusion of a polynucleotide that encodes the molecule, or by use of packaging systems that provide targeting molecules. Those skilled in the art will know, or will ascertain with the use of the teaching provided herein, which molecules and procedures will be useful for delivery of the therapeutic reagent to specific tissues.

EXAMPLES

The following examples are put forth so as to provide those of ordinary skill in the art with a complete disclosure and description of how to carry out the invention and are not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is average molecular weight, temperature is in degrees Centigrade, and pressure is at or near atmospheric.

Example 1

Molecular Cloning of the Mouse ank Gene

The ank gene was mapped isolated and sequenced using techniques as described below.

Mice

Mus castaneus and ank mice were obtained from the Jackson Laboratory (Bar Harbor, Me.). In order to narrow the position of the ank mutation to a small genetic region of mouse chromosome 15, Mus castaneus and ank mice were bred to generate F1 hybrid animals. The F1 hybrids were intercrossed to generate a total of 4,138 F2 progeny. All F2 progeny were screened at 5 weeks of age for the ability to grip a wire cage grid. The 923 progeny showing the ank phenotype were sacrificed by $CO_2$ inhalation. Alizarin red stained skeletons were prepared using a modified version of a method described (Green, *Ohio J Sci.*, 52:31–33 (1952)). DNA samples for use in the typing of the 923 affected animals were prepared as described (Couse et al., *Biotechniques*, 17:1030–2 (1994)).

Initially, a small number of progeny were typed with a number of genetic markers previously assigned to mouse chromosome 15, including D15Mit11, D15Mit12, D15Mit13, D15Mit34 D15Mit54, D15Mit55, D15Mit90, D15Mit184, D15Mit228, D15Mit251, and D15Mit262. These studies showed that the ank mutation was located between D15Mit251 and D15Mit55. To identify animals with informative recombination events located between these markers, all F2 animals showing the ank phenotype were subsequently typed with both D15Mit251 and D15Mit55. Most progeny showing the ank mutant phenotype were homozygous for the D15Mit251 and D15Mit55 alleles characteristic of the original ank mouse strain. A small number of animals showed inheritance of both ank-like and M castaneus-like alleles at one or the other of the loci (77 out of 1846 meiosis), and thus inherited a recombinant chromosome with a crossover located between D15Mit251 and D15Mit55. Such animals were subsequently typed with 26 additional DNA markers, including D15Mit226, D15Mit111, D15Mit109, D15Mit200, D15Mit267, D15Mit110, D15Mit127, D15Mit135, D15Mit9, D15Mit253, D15Mit201, D15Mit180, D15Mit98, D15Mit21, D15Mit18, D15Mit82, D15Mit163, D15Mit45, D15Mit131, D15Mit38, D15Mit130, D15Mit203, D15Mit204, D15Mit202, and D15Mit164 and D15Mit20. The D15Mit164 and D15Mit20 markers failed to recombine with the ank phenotype in any of the F2 progeny analyzed (0 recombination events in 1846 total meiosis). D15Mit20 was used as a molecular entry point to initiate a chromosome walk in the ank nonrecombinant region.

Marker Isolation and Typing

Microsatellite markers were typed on individual DNA samples by combining 100–300 ng of genomic DNA with 1×TKG (10 mM Tris pH 8.3, 50 mM KCl, 0.001% gelatin), 2 mM $MgCl_2$, 0.2 mM dNTP, 100 nM of each SSLP primer (Research Genetics), 0.5U of Amplitaq polymerase (Perkin Elmer) and 1 μCi of $^{32}$P-dCTP to a total volume of 20 μl. Each reaction was overlaid with 50 μl of mineral oil and denatured at 94° C. for 3 min, then cycled 33 times at 94° C. 1 min, 55° C. min, 72° C. 1 min with a final extension temperature of 72° C. for 10 min on a PTC-100 Thermal Controller (MJ Research). Reactions were then diluted 1:3 with Formamide gel loading dye (Sambrook et al., *Molecular Cloning: a Laboratory Manual*, (2 ed.) (Cold Springs Harbor, N.Y., Cold Spring Harbor Laboratory Press) (1989)), and 4 μl of this dilution were loaded onto a 6% polyacrylamide gel and detected by autoradiography.

Mouse BAC Screen

A Bacterial Artificial Chromosomes (BAC) screen was initiated by using the non-recombinant SSLP primer D15Mit20 on the Research Genetics CITB Mouse BAC DNA Pools Release II (Research Genetics, Huntsville, Ala.). PCR conditions described previously for marker isolation and typing were used for the primary and secondary screen. The tertiary screen was done by hybridization using a BAC end probe from BAC 110P8 generated by the previously described bubble PCR method (Riley et al., *Nucl. Acid. Res*, 18:2887–2890 (1990)). BAC 282M13 was ordered, streaked and checked for the correct insert.

End probes from BACs were recovered with a modified version of a previously described bubble PCR technique (Riley et al., *Nucl. Acid. Res*, 18:2887–2890 (1990)). The T7 (5'-AAAACGACGGCCAGTGAATTGTAATACGACT-3') (SEQ ID NO:17) and the Sp6 (5'-CATGATTACGC-CAAGCTATTTAGGTGACACT-3') (SEQ ID NO:18) sites of the BAC vector were used to generate the end probes. Restriction fragment length polymorphisms were detected by Southern blot analysis using common methods.

Screening a commercially available bacterial chromosome (BAC) library identified a total of 5 clones that were positive for D15Mit20. End probes from these BACs were recovered using bubble PCR (supra) and tested for recombination with the ank phenotype in the high resolution genetic mapping panel. Both probes recognized restriction fragment length polymorphisms (RFLPs) that failed to recombine with the ank phenotype in any of the F2 offspring. Additional BAC clones were therefore isolated using the new end probes to extend the chromosome walk. After 2 additional rounds of library screening and end probe isolation, a series of overlapping BAC clones were identified that completely spanned the chromosome interval containing the ank mutation. A probe isolated from one end of this overlapping set recognized an RFLP that recombined 2 times with the ank phenotype in the high resolution mapping panel. A probe identified from the other end of the contig recognized an RFLP that recombined 3 times with the ank phenotype in the high resolution mapping panel. The genetic data indicate that the ank mutation was located within the chromosome segment defined by these clones.

Construction of Sequencing Library

BAC DNA was isolated by equilibrium centrifugation in a cesium chloride—ethidium bromide gradient, resuspended in 100 mM Tris pH 8.0, 1 mM EDTA, 50% glycerol, and sheared mechanically through a 27½ gauge needle at room temperature for 2 hr to produce fragments ~2 to 3 kb in length. The sheared BAC fragments were purified on a 0.8% agarose gel, extracted and eluted in water with the Geneclean II kit (BIO101), and subcloned into the pBluescript SK(+) vector (Stratagene) at the EcoRV site by blunt end ligation. To identify ligated products containing BAC inserts, DH10B cells were electroporated with an aliquot of the ligation reaction and subjected to blue/white selection on an LB-ampicillin X-gal plate. Cells from white colonies of these plates were inoculated into tubes containing 4 ml of LB-ampicillin medium and grown for 16 hours at 37° C. Plasmid DNA from these cultures was isolated and eluted in 50 µl water using the Ultraclean mini plasmid prep kit (McFrugal's Lab Depot), and presence of the subcloned BAC insert Divas verified by an XhoI-XbaI digest of the plasmid DNA. Typically, about 80% of selected clones contained inserts of the expected size.

Random Sequencing and Identification of Candidate Genes on BAC 282-M-13

Subcloned BAC fragments were sequenced from both ends using T3 (5' AATTAACCCTCACTAAAGG 3') (SEQ ID NO:19) and T7 (5' GTAATACGACTCACTATAGG 3') (SEQ ID NO:20) primers with the ABI Prism Dye Terminator Cycle Sequencing Kit (PE Applied Biosystems) in the following 5 µl reaction: 1.5 to 2.5 µl plasmid DNA, 0.5 µl primer at 1.6 µM (0.8 pmol), 2 µl FS enzyme mix (PE Applied Biosystems), and water to bring the final volume to 5 µl. Reactions were overlaid with mineral oil and cycled on a PTC-100 Thermal Controller (MJ Research) for 26 cycles at 96° C. for 12 seconds, 50° C. for 15 seconds, and 60° C. for 4.5 minutes. The reaction products were then precipitated with 0.3 M sodium acetate pH 5.2 and 3 volumes of ethanol, resuspended in 1.6 µl of 83% formamide/17% blue dextran-EDTA, and run on an ABI Prism 377 DNA Sequencer (PE Applied Biosystems). Random sequencing of BAC282-M-13 identified a total of 450 kb of trimmed sequences corresponding to approximately ~2x sequence coverage.

The portion of each sequence that was derived from the pBluescript vector was trimmed away, and the remaining sequences were submitted for homology searches in the Genbank and Expressed Sequence Tag (EST) databases at the National Center for Biotechnology Information. Database searches of the resulting sequence identified eleven mouse cDNA groups that showed strong homology to the sequences from BAC 282. One of these groups was a mouse cDNA clone isolated from mitogen-stimulated prostate carcinoma cells; another was a ribosomal protein subunit; and the rest were anonymous. None of the groups identified suggested any relation to the progressive ankylosis trait or arthritis susceptibility.

Identification of ank Defect

To test for possible mutations in candidate genes, primers were designed to amplify the coding regions from RNA of wild type mice and animals homozygous for the ank mutation. These studies identified a G to T mutation in one of the candidate genes in ank mutant animals, at position 1348 of the sequence shown as SEQ ID NO:15. This nucleotide change destroys an existing Hinf1 site in the corresponding nucleotide sequence.

Primers were designed to amplify the corresponding region from genomic DNA samples. Hinf1 digestion of the amplified region confirmed the presence of the mutation in genomic DNA of ank mutant animals. A survey of 25 different mouse strains by amplification and Hinf1 digestion showed that the sequence change was not found in any other strains, and therefore is not a simple polymorphism. Importantly, this sequence alteration was also not found in the wild type strains from which the ank mutation arose. These data show that this base pair change is specific to the ank mutant stock, and is likely to represent the site of the ank mutation. The gene disrupted by this sequence change was named "ank" gene in conformance with previous genetic nomenclature in mice, and the predicted protein product of the gene is referred to as ANK.

Amplification and Sequencing of the Murine ank Gene

Total brain RNA was isolated by RNAzol extraction (Tel-test) from a male 2-month-old ank/ank mouse as well as from age- and sex-matched C57BL/6, C57BL/10, and C3H strains which are wild type at the ank locus. ank cDNA was synthesized by denaturing 3 µl of RNA, 2 µl $R_0$ primer (5' TAGGAAATGTATTATAGCCTAA 3') (SEQ ID NO:21) at 20 µM, and 5 µl DEPC water for 8 min at 65° C. followed by reverse transcription at 52° C. for 1 hr in a reaction containing the denatured RNA/primer plus 4 µl 5x cDNA buffer (GibcoBRL), 1 µl 0.1 M dithiothreitol, 1 µl 40 U/µl RNAseOUT (GibcoBRL), 1 µl DEPC water, 2 µl 10 mM dNTP (GibdoBRL), and 1 µl 15 U/µl Thermoscript reverse transcriptase (GibcoBRL). The reaction was terminated by a 5-min incubation at 85° C., and the RNA was removed by 1 µl 2 U/µl RNAse H at 37° C. for thirty minutes. The ank open reading frame was amplified using 2 µl of the reverse transcription product as template in a PCR reaction containing 5 µl of 10x PCR buffer (GibcoBRL), 1 µl 50 mM $Mg_2SO_4$, 1 µl 10 mM dNTP, 1 µl $F_1$ primer (5' TGAGT-GTGGGGTCAGCCCAC 3') (SEQ ID NO:22), 1 µl $R_1$ primer (5' ACTTTGACTAAATCAGGAATT 3') (SEQ ID NO:23), 2.5 U High Fidelity Platinum Taq DNA polymerase (GibcoBRL), and water to 50 µl, followed by a second round of hemi-nested PCR reaction containing 10 µl 10x cloned Pfu buffer (Stratagene), 2.5 µl 10 mM dNTP (GibcoBRL), 2.5 µl $F_1$ primer, 2.5 µl $R_2$ primer (5' TAGTGAACTGT-GTCCATAATR 3') (SEQ ID NO:24), 5 U Pfu turbo DNA polymerase (Stratagene), 1 µl primary PCR reaction product as template, and water to 100 µl. PCR reactions were denatured at 94° C. for 2 min 15 sec and cycled 33 times at 94° C. (30 sec), 52° C. (1.5 min), 68° C. (4 min 15 sec) for the primary reactions and 94° C. (1 min), 52° C. (1.5 min), 72° C. (4.5 min) for the secondary reaction, followed by a 10 min incubation at the extension temperature. Secondary PCR products were purified on a 1% low-melt agarose gel (FMC Bioproducts), extracted and eluted in water with the UltraClean Gelspin DNA purification kit (McFrugal's Lab Depot), and 30–50 ng were sequenced with the ABI Prism BigDye Terminator Cycle Sequencing Kit (PE Applied Biosystems) in a reaction containing 5.5 µl 2.5× buffer (200 mM Tris pH 9.0, 5 mM $MgCl_2$), 2 µl sequencing primer at 1.6 µM, 2.5 µl enzyme mix (PE Applied Biosystems), and water to 20 µl with conditions described above. The sequencing primers used were:

$F_1$ (SEQ ID NO:22)

$F_2$ (5' GGGTACTACATCATCAACAA 3'), (SEQ ID NO:25)

$F_3$ (5' TGGCTCTGATCCTGGCCACG 3'), (SEQ ID NO:26)

$F_4$ (5' CCAGTGCCAGTGACTGTGAG 3'), (SEQ ID NO:27)

$F_5$ (5' GTCAGGACAACAACTGTCGT 3'), (SEQ ID NO:28)

$F_6$ (5' AACTATCTGCCGCACATACT 3'), (SEQ ID NO:29)

$F_7$ (5' TGCCAGGGTCTTGTCTCGTA 3'), (SEQ ID NO:30)

$R_2$ (SEQ ID NO:24)

$R_3$ (5' AACGAAATGGACAGTTAGAG 3'), (SEQ ID NO:31)

$R_4$ (5' GGAGCAAGTCAAGAGAGGCT 3'), (SEQ ID NO:32)

$R_5$ (5' GCAGCCTGTGCTTACTCATT 3'), (SEQ ID NO:33)

$R_6$ (5' GGCAAAGTCCACTCCAATGA 3'), (SEQ ID NO:34)

$R_7$ (5' CAGCTCTGGGCCGCTCCTGT 3'), (SEQ ID NO:35) and $R_8$ (5' TCAGGGTGTGGAAGACGGCA 3'). (SEQ ID NO:36)

Raw sequences from wildtype and mutant samples were imported into the Sequencher program (Gene Codes Corporation) and compared. To verify the sequence change observed in the ank mutant allele at the genomic level, a 58 bp region containing the mutation site was amplified from wildtype and mutant genomic DNA in a PCR reaction containing 10 µl cloned Pfu buffer (Stratagene), 1.25 µl 20 mM dNTP (Pharmacia), 2.5 µl $M_1$ primer (5' GGCTCCCTTCTAGCAGGGTT 3') (SEQ ID NO:37) at 20 µM, 2.5 µl $M_2$ primer (5' AGCATGCTGCAAGGGCAACC 3') (SEQ ID NO:38) at 20 µM, 5 U Pfu turbo DNA polymerase (Stratagene), 1 µl genomic DNA as template, and water to 100 µl, and the presence of the mutation was assayed by Hinfl restriction digest of the PCR products.

Exon/Intron Structure of the Murine ank Gene

The large scale sequencing project of BAC 282-M-13 identified 27 clones that contained parts of the ank open reading frame. Sequences from these clones were imported into the Sequencher program and assembled into a contiguous genomic sequence of the mouse ank gene which was compared to the mouse ank cDNA sequence to identify the exon/intron boundaries of the gene as well as the intronic sequences flanking the exons.

Structure of the ANK Protein

The largest open reading frame of the ank mouse gene is predicted to encode a protein of 492 amino acids (SEQ ID NO:16). Hydrophobicity analysis with the Kyte Doolittle algorithm revealed the presence of a number of stikingly hydrophobic stretches in the ANK protein. Most of these were approximately 20 residues long, as expected for transmembrane spanning regions in a multiple-pass integral membrane protein. The base pair change in ank mutant mice changes a glutamine codon into a stop codon at position 410 of the corresponding protein (SEQ ID NO:16). This change would block formation of the wild type ANK protein in mutant mice, and lead to production of a shortened protein missing 53 amino acids from the C terminus.

Example 2

Molecular Cloning of Human ank Gene

The characterization of the mouse gene and its intron/exon structure assisted in the identification of a related human version of the ank gene, and allowed the determination of the coding sequence and intron/exon structure of the human gene.

The CITB Human BAC DNA Pools (B&C) Release IV Library (Research Genetics, Huntsville Ala.) was screened by PCR with 1×PCR buffer (Perkin Elmer), 2 mM $MgCl_2$, 0.1985 mM dNTP, 1.3 µM of R110 dUTP and R6GdUTP (PE Applied Biosystems), 8 µM of forward primer 5'-TGTAGCCATTTTGCTTCACAGT-3' (SEQ ID NO:39), 8 µM of reverse primer 5'-AGCTCGGGGCCACTTCTGT-3' (SEQ ID NO:40), and 0.5U of Amplitaq polymerase (Perkin Elmer) to a total volume of 20 µl. The reactions were denatured at 94° C. for 3 min, then cycled 33 times at 94° C. for 40 sec, 60° C. for one min and 72° C. for 40 sec with a final extension time of 10 min at 72° C. on a PTC-100 Thermal Cycler (MJ Research). 1.5 µl of the PCR product mixed with 2.5 µl of deionized formamide (Gibco-BRL), 0.5 µl of ROX size standard, and 0.5 µl of Loading buffer (PE Applied Biosystems). 1 µl of this mix was loaded onto a 5% polyacrylamide gel (FMC, Catalog # 50691) and run on an ABI Prism 377 using the Genescan program. BAC 364E20 and 571E1 were ordered, streaked out, and tested for the correct insert by PCR. These two BACs appeared to be missing exons one through four.

Another BAC screen was also performed to isolate the 5' end of the human ank gene. The same BAC library was screened by PCR with 1×PCR Buffer (Perkin Elmer), 1.5 mM $MgCl_2$, 0.2 mM dNTP, 0.4 µM of forward primer (5'-Hex-GCATTGCTGCTGTCAAGGAG-3')(SEQ ID NO:41), 0.4 µM of reverse primer (5' Hex-TGCTGTTCACAAACACCAGG-3')(SEQ ID NO:42), and 0.5U of Amplitaq polymerase (Perkin Elmer) to a total volume of 20 µl. The reactions were denatured at 94° C. for 3 minutes, then cycled 33 times at 94° C. for 40 sec, 58° C. for one min and 72° C. for 40 sec with a final extension temperature of 72° C. for 10 min on a PTC-100 Thermal Cycler (MJ Research). 1 µl of PCR reaction was mixed with 2.0 µl of deionized formamide (Gibco BRL), 0.5 µl of TAMRA size standard and loading buffer (PE Applied Biosystems). 1 µl of this mix was loaded onto a 5% polyacrylamide gel (FMC, Catalog # 50691) and run on an ABI Prism 377 using the Genescan program. BAC 510N16 was ordered, streaked out, and tested for correct insert by PCR.

Exon/Intron Structure of the Human ank Gene.

The exon/intron boundaries for exons 2–4, 5, and 7–9 were determined bad sequencing bubble PCR products from BAC 510N 16 and 364E20 respectively. The amplification reactions for each exon used two gene specific primers that were designed based on the predicted location of exons in the mouse gene, and a Universal PCR primer (5'-CGAATCGTAACCGTTCGTACGAGAATCGCT-3')(SEQ ID NO:43) (Riley et al., *Nucl. Acid Res,* 18:2887–2890 (1990)). All PCR products were run on a 1.0% agarose gel, gel isolated, (Doc Frugals' Gel Spin Kit), and cloned into the Original TA Cloning Vector (Invitrogen). Protocols for the ligation, transformation, and plating were followed according to Invitrogen's instructions.

White colonies were picked and grown overnight in 2–5 mls of LB-AMP (50 mg/ml) liquid medium, then miniprepped using common methods. Minipreps were checked for the correct insert size by cutting the insert from the vector by restriction digest. Correct inserts were sequenced on the ABI Prism 377 machine using methods previously described with M13 forward (5'-GTAAAACGACGGC-CAGTG-3') (SEQ ID NO:44) and reverse (5'-GGAAA-CAGCTATGACCATG-3') (SEQ ID NO:45) primers. The gene specific primers used were as follows:

| Exon | Forward Primer 5'-3' | |
|---|---|---|
| 2 | GCATTGCTGCTGTCAAGGAG | (SEQ ID NO:41) |
| 3 | AGCAAGACGAGAAGGGCCTT | (SEQ ID NO:46) |
| 4 | GACCCATGCTGGCATTCTCT | (SEQ ID NO:48) |
| 5 | CTGGCTACTACAAGAACATTCACGAC | (SEQ ID NO:50) |
| 7 | GCGATTTTGACAGCCACATACCCTG | (SEQ ID NO:52) |
| 8 | AACCCCAGCAACAAACTGGTGAGCAC | (SEQ ID NO:54) |
| 9 | CTGTTTCGTGATGTTTTGGACACCC | (SEQ ID NO:56) |

| Exon | Reverse Primer 5'-3' | |
|---|---|---|
| 2 | TGCTGTTCACAAACACCAGG | (SEQ ID NO:42) |
| 3 | AAGGCCCTTCTCGTCTTGCT | (SEQ ID NO:47) |
| 4 | ATGACATCTGAGATTGAGGC | (SEQ ID NO:49) |
| 5 | CACTTCTGTCAGGGATGATGTCGTG | (SEQ ID NO:51) |
| 7 | TTGTCGAAAGCAGGATACACAGCAC | (SEQ ID NO:53) |
| 8 | TGAGTGACAGAGCCATGCAGACGAAG | (SEQ ID NO:55) |
| 9 | TGGAACTGGGAAGAAGGAGAAGATC | (SEQ ID NO:57) |

Exon/intron boundaries for exons 6 and 10–12 were determined by sequencing fragments from a restriction digest library from BACs 364E20 and 571E1. Glycerol stocks of both BACs were grown in 500 ml of LB-Chloramphenicol (12 µg/ml) for 12–16 hours at 37° C. The cultures were cesium chloride purified and used for restriction digests. 7–10 µg of BAC DNA was digested for 2 hours with SmaI, BamHI, EcoRV, and PstI separately. Digests were phenol/chloroform extracted, sodium acetate-ethanol precipitated, and resuspended in water. Ligation reactions were composed of 10 µg of Bovine Serum Albumin, 400U of T4 DNA ligase (New England Biolabs), 5–7 µg of digested BAC, and 1 µg of digested pBluesccript KS+. Ligations were done at 15° C. for 11.5 hours. 2 µl of ligation mixture was added to 50 µl of DH10B electrocompetent cells and put on ice for 1 minute. Cells were electroporated and rocked at 37° C. for one hour with 1 ml of SOC broth. Cells were then plated onto LB-AMP (50 µg/ml) plates and grown overnight at 37° C. Plates were then lifted onto Optitran Supported Nitrocellulose filters (Schliecher & Schuell) and prepared for hybridizations using common methods. The mouse ank cDNA was radiolabeled with $^{32}$P-dCTP and hybridized at 65° C. overnight. Filters were washed with 1XSSC, 0.1% SDS for one hour at 65° C. and put on film overnight. Positive colonies were picked and grown in 1–2 mls of LB-AMP (50 µg/ml) overnight; then miniprepped and analyzed for insert. Clones with inserts were sequenced using T3 (5-CAATTAACCCTCACTAAAGG-3') (SEQ ID NO:58) and T7 (5'-GTAATACGACTCACTATA-3') (SEQ ID NO:59) on an ABI Prism 377 machine. Clones that gave exon/intron sequences for exons are as follows:

| | |
|---|---|
| Exon 6 | 364E20 SmaI and BamHI |
| Exon 10 | 364E20 EcoRV |
| Exon 11 | 571E1 BamHI |
| Exon 12 | 364E20 PstI |

The sequence for exon 1 was determined by 5' RACE (Rapid Amplification of cDNA Ends) according to manufacturer's instructions (Gibco-BRL). 4 µg of human U2OS cell total RNA was used for the reactions; the RNA was DNAse treated prior to use. A primer from exon 3 (5'-AAGGCCCT-TCTCGTCTTGCT-3') (SEQ ID NO:60) was used for the first strand cDNA synthesis. A primer from exon 2 (5'-TCCTTGACAGCAGCAATGCCC-3')(SEQ ID NO:61) was used for the first round of PCR; and a second primer from exon 2 (5'-ACAGCAATGCCCCGGTTCAAGGC-3') (SEQ ID NO:62) was used for the secondary PCR. The PCR conditions were 1×PCR buffer, 2 mM MgCl$_2$, (Perkin Elmer), 0.2 mM dNTP mix (Pharmacia), 0.4 µM of exon 2 primer, 0.4 µM of Abridged Primer (Gibco-BRL), and 2.5U of Amplitaq polymerase (Perkin Elmer). The reactions were denatured for 2 min at 94° C., then cycled 33 times at 94° C. for 45 sec, 55° C. for 45 sec and 72° C. for 90 sec. Reactions were then extended for 72° C. for 7 min. 10 µl of primary PCR product were run on a 1.0% agarose gel to visualize products. Once products were confirmed, a secondary PCR was performed on 1 µl of straight and 1:10 diluted primary PCR product. The PCR conditions were 1×PCR buffer, 2 mM MgCl$_2$, (Perkin Elmer), 0.2 mM dNTP mix (Pharmacia), 0.4/µM of exon 2 primer, 0.4 µM of AUAP (Gibco-BRL), and 2.5U of Amplitaq polymerase (Perkin Elmer). The reactions were cycled as in the primary PCR. 25 µl of the secondary PCR reaction was run on a 1.0% agarose gel. The 300 base pair band was cut out and gel purified as described above. Ligation, transformation, plating, picking, growing, miniprepping and sequencing were done as previously described, using the Original TA Cloning Vector (Invitrogen).

The predicted human ANK protein product displays 98% amino acid identity with mouse ANK over its entire length. The positions of the exon/intron boundaries were identical in the mouse and the human genes. The high degree of conservation suggests that the mouse and human genes serve an evolutionarily conserved function in mammals.

Example 3

In vitro Assay for ank Therapeutic Agents

Either in vitro or in vivo assays are used to monitor the efficacy of potential therapeutics in modulating ANK activity. In vitro studies show that levels of intracellular or extracellular pyrophosphate can be used as biological markers of ANK activity in cells or tissues prepared from wild type or ank mutant mice, or animals treated with various therapeutic agents.

In in vitro assays, overexpression of the wild type ANK gene product causes a dramatic reduction in intracellular pyrophosphate levels and an increase in extracellular pyrophosphate levels in tissue culture cells; thus levels of intracellular and extracellular pyrophosphate can be used as surrogate markers for such assays. Abnormal regulation of pyrophosphate levels may explain the pathologic mineralization and destruction seen in joints of ank mutants, as inorganic pyrophosphate and its derivatives have been shown to be potent inhibitors of calcification, bone mineralization, and bone resorption (Fleisch, H., *Metab. Bone Dis. Relat. Res.*, 3:279–87 (1981)).

Several protocols have previously been developed for measuring inorganic pyrophosphate in biological samples and any number of these are used in the in vitro assay. Some measure pyrophosphate hydrolysis to orthophosphate by calorimetry (McCarty et al., *J. Lab. Clin. Med.*, 78:216–29 (1971)), while others use labeled substrates that couple with pyrophosphate in enzymatic reactions to determine pyrophosphate levels radiometrically (Cheung and Suhadolnik, *Anal. Biochem.*, 83:61–3 (1977); Caswell and Russell, *Biochim. Biophys. Acta*, 847:40–7 (1985)). In another type of protocols, inorganic pyrophosphate is subjected to a series of coupled enzymatic phosphorylation and reduction to yield NADPH which can be quantified flourimetrically (Lust and Seegmiller, *Clin. Chim. Acta*, 66:241–9 (1976)). Although each of these can be used in the assay, the latter protocol is used with described modifications as follows.

COS cells grown in DMEM supplemented with 10% fetal bovine serum, 2 mM GlutaMax (Gibco), 0.1 mM non-essential amino acids, 100 units/ml Penicillin G, and 100 μg/ml Streptomycin are harvested and ~1–2×$10^6$ cells are plated on a 100 mm tissue culture dish and incubated overnight at 37° C., 5% $CO_2$. The cells are then transfected with 5 μl of a control cytomegalovirus promoter-driven expression vector or the same vector containing the coding region of the wildtype ank gene using the Lipofectamine Plus (Gibco-BRL) protocol according to manufacturer's instructions. 36 to 48 hours later, $10^6$ to $10^7$ cells are removed from dishes with a rubber policeman, pelleted by centrifugation at 1700×g, washed in 10 ml phosphate-buffered saline pH 7.2 (PBS), and resuspended in 0.5 ml cold PBS. A small aliquot of cells (10 μl) is removed for counting, and inorganic phosphate is extracted from the rest by addition of 47 μl of 70% perchloric acid with rapid vortexing, followed by centrifugation in 2000×g at 4° C. for 10 min to pellet insoluble cellular debris. The supernatent is then neutralized with 4M KOH to pH 7.0 to 8.0, and the resulting $KClO_4$ precipitate is removed by centrifugation at 2000×g for 3 min at 4° C.

To determine the pyrophosphate content of the cellular extract, 75 μl of the extract is incubated at room temperature (20° C. to 22° C.) for 30 min in a reaction containing 25 μl 0.1 M potassium phosphate buffer pH 8.0, 8.3 μl 0.05 M Tris acetate (TA) buffer, 5 μl 0.1 M magnesium acetate in 0.05 M TA buffer, 5 μl 8 mg/ml UDPG in 0.05 M TA buffer, 5 μl 8 mg/ml NADP in 0.05 M TA buffer, 0.28 U phosphoglucomutase (EC 5.4.2.2), 0.28 U glucose-6-phosphate dehydrogenase (EC 1.1.1.49), 0.28 U 6-phosphogluconic dehydrogenase (EC 1.1.1.44), 0.125 U UDPG pyrophosphorylase (EC 2.7.7.9), and deionized water to 250 μl. Blank controls are prepared for each sample by replacing UDPG pyrophosphorylase with water. After the 30 min incubation, the reaction is stopped by addition of 2 ml diluent solution (1.1 g sodium bicarbonate, 2 g sodium carbonate, 0.3 g EDTA in 1 L water, pH adjusted to 10 with glacial acetic acid). Fluorescence of each sample is read in a Sim-Aminco Bowman Series 2 flourimeter with the excitation wavelength at 335 nm, emission wavelength at 455 nm, and bandwidths of 4 to 8 nm. Relative fluorescence contributed by NADPH formed in each sample is calculated by subtracting the reading of the blank control and the fluorescence contributed by UDPG pyrophosphorylase from the sample reading, and the amount of inorganic pyrophosphate is determined by comparing the reading to a standard curve established from control reaction samples with known amounts of sodium pyrophosphate added.

All enzymes and reagents are purchased from Sigma, with the exception of NADP and UDPG which are from Calbiochem, and perchloric acid which is from EM Science. Typical intracellular pyrophosphate values for COS cells transfected with the control vector range from ~100–150 pmol/$10^6$ cells. In contrast, cells transfected with the ANK expression construct show a drop in intracellular pyrophosphate to undetectable levels.

Example 4

In vivo Assay for ank Therapeutic Agents

Efficacy of ANK therapeutics is determined in vivo by measuring the effect that a therapeutic (e.g., a candidate compound) has on expression levels of ANK protein or ank mRNA in animal tissues, using standard procedures. In brief, a candidate compound is administered to an ank/ank animal, and the effect of this candidate compound on the phenotype, gene expression, or protein production assayed. Changes in levels of ANK protein or RNA is determined by Western blotting or radioimmunoassay for ANK protein and Northern blotting or quantitative RT/PCR forank message.

In addition, the effects of potential therapeutic agents can be tested on the tissue mineralization and joint disease phenotypes seen in animals carrying the ank mutation. After exposure to a given therapeutic (genetic, biochemical, pharmacological, or otherwise), animals are quickly assayed for the flexibility of their digits by examining their ability to hold onto a wire grid, or by measuring the maximum angle to which the digits bend upon passive manipulation (see for example, Hakim et al. 1984). The extent of phenotypes in skeletal and soft tissues are determined in histological sections stained with standard procedures, for example, hematoxylin and eosin, fast green-Safranin O for general histology of soft and skeletal tissues, or von Kossa's stain (Kossa, J. V., *Beitr. Path. Amat.*, 29:163–202 (1901)) and Alizarin red staining for measuring phosphate and carbonate or calcium accumulation, respectively. Semi-quantitative scales have already been established for scoring ank phenotypes in sections of this type (See e.g., Krug et al., *Arthritis Rheum.*, 36:1603–11 (1993)). Pyrophosphate levels could also be measured in biological tissues or fluids of mice using the methods described above.

Example 5

Screening for Mutations in Human ank that are Associated With Human Diseases of Mineral Deposition and Susceptibility to Arthritis The nucleotide sequence and exon/intron boundaries of the human ank gene (see example 2 and SEQ ID NOS:3–14) are in many different assays for mutations in the human ank gene. These assays have value as diagnostic and/or prognostic indicators in individuals displaying either excessive or inadequate mineral deposition.

The ank sequences are used to design primers and PCR assays for amplification of ank coding exons and exon/intron boundaries from human genomic DNA. Primers located in the 5' and 3' untranslated regions of the human ank gene are used to recover ank cDNA from RNA samples prepared from human cells, for example blood cells, Ebstein-Barr virus-transformed lymphoblasts, or cultured skin fibroblasts.

Primer amplification conditions that were successfully used to recover ank exons are as follows.

Amplification of Human ank Exons 2, 4, 5, 7, 11 and 12

To survey for possible mutations in the open reading frame, splice junctions, and branchpoints of the ank gene in families with known arthritic disease, the human ank exons and surrounding intron sequences were amplified from genomic DNA of both unaffected and affected patients of these families by two rounds of PCR. The primary round of PCR was carried out using 100–250 ng genomic DNA as template in a reaction containing 5 µl 10× cloned Pfu buffer (Stratagene), 0.625 µl 20 mM dNTP (Pharmacia), 1.25 µl 20 µM primary forward primer (1F), 1.25 µl 20 µM primary reverse primer (1R), 2.5 U Pfu turbo DNA polymerase (Stratagene), and water to 50 µl. PCR reactions were denatured at 94° C. for 2 min 15 sec and cycled 33 times at 94° C. (1 min), 58° C. (1.5 min), and 72C (1 min), followed by a 10 min incubation at 72° C. 1 µl of this primary PCR product was then used as template in a second round of hemi- or full-nested PCR reaction with identical reagents and cycling conditions as those in the primary reaction except secondary forward (2F) and reverse (2R) primers were used in lieu of the primary primer set. Primary and secondary PCR products were electrophoresed on a 2% agarose gel and examined for possible changes in band patterns between unaffected and affected samples. Sequences of the primer sets used for amplifying the exons are as follows:

| Exon 2 | | |
|---|---|---|
| 1F | AACTGAAGCTGATGTAGATGAA | (SEQ ID NO:63) |
| 1R | ATCGCTGTCCTCTCCTTAAAT | (SEQ ID NO:64) |
| 2F | AACCAATCACCTTTATCCAATTA | (SEQ ID NO:65) |
| 2R | TTGCCAAAGCTAGATTCGTCA | (SEQ ID NO:66) |

| Exon 4 | | |
|---|---|---|
| 1F | CACCAGATCAAGTTACAGTAAT | (SEQ ID NO:67) |
| 1R | ATACTGTTATTACAGGGCATTC | (SEQ ID NO:68) |
| 2F | CACCAGATCAAGTTACAGTAAT | (SEQ ID NO:69) |
| 2R | TGATGTAACGGTGCTGGCAA | (SEQ ID NO:70) |

| Exon 5 | | |
|---|---|---|
| 1F | TCATGGTGGGTATAACAAAATG | (SEQ ID NO:71) |
| 1R | TTCCCTGCAGACATCTAGCA | (SEQ ID NO:72) |
| 2F | CCATGTTCCTCCAGTGAATC | (SEQ ID NO:73) |
| 2R | ATGACATCCTGGCCAACTTC | (SEQ ID NO:74) |

| Exon 7 | | |
|---|---|---|
| 1F | GTTCGTACGAGAATCGCTGT | (SEQ ID NO:75) |
| 1R | CATCCTGGGATCAGCGTCA | (SEQ ID NO:76) |
| 2F | TTGTCACCCAGTGTAGCGG | (SEQ ID NO:77) |
| 2R | CAACGTCACATTAACCTTACAA | (SEQ ID NO:78) |

| Exon 11 | | |
|---|---|---|
| 1F | CTACACTTACTTTCCTGGGTT | (SEQ ID NO:79) |
| 1R | CAGTGGCTGCTCAGGTTCT | (SEQ ID NO:80) |
| 2F | CATCGACGGTTGTGCCTTG | (SEQ ID NO:81) |
| 2R | CTGCACCCAGGAGGATGC | (SEQ ID NO:82) |

| Exon 12 | | |
|---|---|---|
| 1F | GAAGGTTTAAGCCTACAGTGA | (SEQ ID NO:83) |
| 1R | TGATGCCGAAGTGTCATCCT | (SEQ ID NO:84) |
| 2F | GAAGGTTTAAGCCTACAGTGA | (SEQ ID NO:85) |
| 2R | GACTGACTGTCCCTGCAGT | (SEQ ID NO:86) |

Sequencing of Human ank Exons 2, 4, 5, 7, 11, and 12:

Secondary PCR products were purified on a 2% low-melt agarose gel (FMC Bioproducts), isolated and eluted in water with the UltraClean Gelspin DNA purification kit (McFrugal's Lab Depot), and 20 ng were sequenced with the ABI Prism BigDye Terminator Cycle Sequencing kit (PE Applied Biosystems) in a reaction containing 7 µl 2.5× buffer (200 mM Tris pH 9.0, 5 mM $MgCl_2$), 2 µl 1.6 µM sequencing primer, 1 µl enzyme mix (PE Applied Biosystems), and water to 20 µl. The exon sequencing primers used were the secondary PCR primers (2F and 2R) of the corresponding exon as described above. Sequencing reactions were cycled on a PTC-100 Thermal Controller (MJ Research) for 26 cycles at 96° C. (12 sec), 50° C. (15 sec), and 60° C. (4.5 min), precipitated in 0.3 M sodium acetate pH 5.2 and 3 volumes of ethanol, resuspended in 1.6 µl 17% blue dextran-EDTA/83% formamide, and run on an ABI Prism 377 DNA Sequencer (PE Applied Biosystems). Chromatograms and DNA sequences from the ank exons of affected and unaffected patient samples were imported into the Sequencher program (Gene Codes Corporation) and analyzed for anti differences.

Amplification of Human Exons 3, 6, 8, 9, and 10:

The modification, nucleotide primers, and sequencing protocols for the remaining exons are as follows:

Exon 3: Primary PCR was done with 100 ng of genomic DNA combined with DNA 1× buffer (Gibco-BRL), 3 mM MgSO$_4$, 0.4 mM dNTP (Pharmacia), 0.8 µM forward primer (5'-GATGAGATTGTAGATGATTTTT-3') (SEQ ID NO:87), 0.8 µM reverse primer (5'-TGTGAATGTACTTC-CTGCC-3') (SEQ ID NO:88) and 1.25U of High Fidelity Platinum Taq DNA polymerase (Gibco-BRL). Samples were denatured at 94° C. for 2 min, then cycled 33 times at 94° C. for 30 sec; 54° C. for 30 see, and 68° C. for 20 see with a final extension of 68° C. for 10 min.

A secondary PCR was done using 1 µl of the primary PCR reaction combined with DNA 1×PCR buffer (Gibco-BRL), 3 mM MgSO$_4$, 0.4 mM dNTP (Pharmacia), 0.8 µM forward primer (5'-CTATGACGAACAAATACTACATT-3')(SEQ ID NO:89), 0.8 µM reverse primer (5'-AAGCCAAC-GATCTTCTCTAC-3')(SEQ ID NO:90), and 2.5U of High Fidelity Platinum Taq DNA polymerase (Gibco-BRL). Samples were denatured at 94° C. for 2 min then cycled 33 times at 94° C. for 30 sec, 56° C. for 30 sec, and 68° C. for 20 see with a final extension of 68° C. for 10 min.

Exon 6: Primary PCR was done with 100 ng of genomic DNA combined with DNA 1×PCR buffer (Gibco-BRL), 2.5 mM MgSO$_4$, 0.4 mM dNTP (Pharmacia), 0.8 µM forward primer (5'-GCTTCCAGCCAGTCCATITG-3')(SEQ ID NO:91), 0.8 µM reverse primer (5'-ATCATAAGCCCCA-CATCCC-3')(SEQ ID NO:92), and 1.25U of High Fidelity Platinum Taq DNA polymerase (Gibco-BRL). Samples were denatured at 94° C. for 2 min then cycled 33 times at 94° C. for 30 sec, 56° C. for 30 sec, and 68° C. for 20 sec with a final extension of 68° C. for 10 min.

A secondary PCR was done using 1 µl of the primary PCR reaction combined with DNA 1×PCR buffer (Gibco-BRL), 1.5 mM MgSO$_4$, 0.4 mM dNTP (Pharmacia), 0.8 µM forward primer (5'-TTGGTTAGAGATTCCCCGAG-3') (SEQ ID NO:93), 0.8 µM reverse primer (5'-ATCATAAGC-CCCACATCCC-3')(SEQ ID NO:92), and 2.5U of High Fidelity Platinum Taq DNA polymerase (Gibco-BRL). Samples were denatured at 94° C. for 2 min then cycled 33 times at 94° C. for 30 sec, 56° C. for 30 sec, and 68° C. for 20 sec with a final extension of 68° C. for 10 min.

Exon 8: Primary PCR was done with 100 ng of genomic DNA combined with DNA 1×PCR buffer (Gibco-BRL), 2.5 mM MgSO$_4$, 0.4 mM dNTP (Pharmacia), 0.8 µM forward primer (5'-TCAACATGACAGCCCGCTTG-3')(SEQ ID NO:94), 0.8 µM forward primer (5'-TGAGAAGTCCCAA-GAAATGCCTG-3')(SEQ ID NO:95), and 1.25U of High Fidelity Platinum Taq DNA polymerase (Gibco-BRL). Samples were denatured at 94° C. for 2 min then cycled 33 times at 94° C. for 30 sec, 58° C. for 30 sec, and 68° C. for 20 sec with a final extension of 68° C. for 10 min.

A secondary PCR was done using 1 µl of the primary PCR reaction combined with DNA 1×PCR buffer (Gibco-BRL), 2.5 mM MgSO4, 0.4 mM dNTP (Pharmacia), 0.8 µM forward primer (5'-TCAACATGACAGCCCGCTTG-3') (SEQ ID NO:94), 0.8 µM reverse primer (5'-GTCCCAA-GAAATGCCTGAAGTG-3')(SEQ ID NO:96), and 2.5U of High Fidelity Platinum Taq DNA polymerase (Gibco-BRL). Samples were denatured at 94° C. for 2 min then cycled 33 times at 94° C. for 30 sec, 60° C. for 30 sec, and 68° C. for 20 sec with a final extension of 68° C. for 1 min.

Exon 9: Primary PCR was done with 100 ng of genomic DNA combined with DNA 1×PCR buffer (Gibco-BRL), 4 mM MgSO$_4$, 10% DMSO, 0.4 mM DNTP (Pharmacia), 0.8 µM forward primer (5'-CGGTTGTCCCTCTTTCGTAAC-3')(SEQ ID NO:97), 0.8 µM reverse primer (5'-GGCAT-GAGGATAAACAGGAATG-3')(SEQ ID NO:98), and 1.25U of High Fidelity Platinum Taq DNA polymerase (Gibco-BRL). Samples were denatured at 94° C. for 2 min then cycled 33 times at 94° C. for 30 sec, 60° C. for 30 sec, and 68° C. for 20 sec with a final extension of 68° C. for 10 min.

A secondary PCR was done using 1 µl of the primary PCR reaction combined with DNA 1×PCR buffer (Gibco-BRL), 2 mM MgSO$_4$, 0.4 mM dNTP (Pharmacia)., 0.8 µM forward primer (5'-GCCACACCTGATCTGCTCAATRC-3')(SEQ ID NO:99), 0.8 µM reverse primer (5'-GGCATGAG-GATAAACAGGAATG-3')(SEQ ID NO:98), and 2.5 U of High Fidelity Platinum Taq DNA polymerase (Gibco-BRL). Samples were denatured at 94° C. for 2 min then cycled 33 times at 94° C. for 30 sec, 60° C. for 30 sec, and 68° C. for 20 sec with a final extension of 68° C. for 10 min.

Exon 10: Primary PCR was done with 100 ng of genomic DNA combined with DNA 1×PCR buffer (Gibco-BRL), 3 mM MgSO$_4$, 0.4 mM DNTP (Pharmacia), 0.8 µM forward primer (5'-GCCAGCGGTTCAAAAAAA G-3')(SEQ ID NO:100), 0.8 µM reverse primer (5'-AGACGTGCCTGGG-GATTTC-3')(SEQ ID NO:101), and 1.25U of High Fidelity Platinum Taq DNA polymerase (Gibco-BRL). Samples were denatured at 94° C. for 2 min then cycled 33 times at 94° C. for 30 sec, 54° C. for 30 sec, and 68° C. for 33 sec with a final extension of 68° C. for 10 min.

A secondary PCR was done using 1 µl of the primary PCR reaction combined with DNA 1×PCR buffer (Gibco-BRL), 2 mM MgSO4, 0.4 mM DNTP (Pharmacia), 0.8 µM forward primer (5'-GCCAGCGGTTCAAAAAAAG-3')(SEQ ID NO:100), 0.8 µM reverse primer (5"-GATTTCCCCT-GAAAATGTAGC-3')(SEQ ID NO:102), and 2.5U of High Fidelity Platinum Taq DNA polymerase (Gibco-BRL). Samples were denatured at 94° C. for 2 min then cycled 33 times at 94° C. for 30 sec, 54° C. for 30 sec., and 68° C. for 33 sec with a final extension of 68° C. for 10 min.

To prepare samples for direct sequencing, the secondary PCR reactions were run on a 1.0% agarose gel, gel bands were cut out and cleaned up with a gel spin kit (Doc Frugals Scientific). 1 µl of the eluent was combined with 40 pmol of primer (same ones used in secondary PCR), 7 µl of 2.5× sequencing buffer (200 mM Tris pH 9.0, 5 mM MgCl$_{12}$), 1 µl of Big Dye Terminator Cycle Sequencing Ready Reaction (PE Applied Biosystems) and water up to a final volume of 20 µl. Reactions were cycle sequenced and precipitated as directed by PE Applied Biosystems. Reactions were loaded onto an ABI Prism 377 sequencing machine and analyzed with Sequencher 3.1.

Amplification of Human Exon 1

To confirm the sequence of exon 1, this exon was amplified and sequenced as follows: Primary PCR was performed with 100 ng of genomic DNA combined with DNA 1×PCR buffer (Gibco BRL), 2.5 mM MgSO$_4$, 0.4 mM dNTP, 0.8 µM Forward primer 5'-CATCGGTACCGCTTATATGG-3'(SEQ ID NO:103), 0.8 µM Reverse primer 5'-ACCATTTTCCA-GAGAGGGCT-3' (SEQ ID NO:104), and 1.25 U of High Fidelity Taq polymerase (Gibco-BRL) in 25 µl of water. Samples were denatured at 94° C. for 2 minutes, then cycled 33 times at 94° C. for 30 sec, 56° C. for 30 sec, and 68° C. for 20 sec with a final extension of 68° C. for ten min.

A secondary PCR was done using 1 μl of the primary PCR reaction combined with DNA 1×PCR buffer (Gibco-BRL), 1× DMSO, 2.0 mM MgSO₄, 0.4 mM dNTP, 0.8 μM Forward primer 5'-GATCTTTGTTGTGTGGGAGG-3',0.8 μM Reverse primer 5'-GATAAAGAGGGACTCGGAGC-3', 2.5 U of High Fidelity Taq polymerase (Gibco-BRL) in 50 μl of water. Samples were denatured at 94° C. for 2 min, then cycled 33 times at 94° C. for 30 sec, 58° C. for 30 sec, and 68° C. for 20 sec with a final extension of 68° C. for ten minutes. The final product was applied to Qiagen Cleanup columns, eluted with 30 μl of water, and 25 ng of product was used for sequencing with 40 pmol of primer (same ones used in secondary PCR), 7 μl of 2.5× sequencing buffer (200 mM Tris pH 9.0, 5 mM MgCl₂), 1 Fl of Big Dye Terminator Cycle Sequencing Ready Reaction (PE Applied Biosystems) and water up to a final volume of 20 μl. Reactions were cycle sequenced and precipitated as directed by PE Applied Biosystems. Reactions were loaded onto an ABI Prism 377 sequencing machine and analyzed with Sequencher 3.

Example 6

Identification of SNPs in the ank Gene

SNPs were identified in the ank genomic sequence using die amplification and sequencing methods previously described in EXAMPLE 5. Each of these SNPs introduces a change in an intronic sequence or a silent mutation in a coding region. The following exemplary SNPs were identified:

SNP 1:Either C or T at position 298 in SEQ ID NO:4.
This SNP occurs within the coding region of exon 2. The primers used to amplify this region of the ank gene were SEQ ID Nos: 65 and 66.
Local sequence context to confirm location:
ccatcgctgcNgtcttcaca (SEQ ID NOS:105 and 106)
SNP2: Either G or A at position 326 in SEQ ID NO:4.
This SNP occurs within the 3' intron after exon 2. The primers used to amplify this region of the ank gene were SEQ ID Nos: 65 and 66.
Local sequence context to confirm location:
aggtgaggccNccgaccgcca (SEQ ID NOS:107 and 108)
SNP3: Either G or A at position 50 in SEQ ID NO:7. This SNP occurs within the 5' intron preceding exon 5. The primers used to amplify this region of the ank gene were SEQ ID NOS:73 and 74.
Local sequence context to confirm location:
gcttctgtcaNtcggttcccg (SEQ ID NOS:109 and 110)
SNP4: Either A or G at position 148 in SEQ ID NO:10.
This SNP occurs within the coding region of exon 8. The primers used to amplify this region of the ank gene were SEQ ID NOs:94 and 96.
Local sequence context to confirm location:
cagtcacggcNgcccacatca (SEQ ID NOS: 111 and 112)
SNP5: Either A or G at position 220 in SEQ ID NO:8.
This SNP occurs within the 5' intron preceding exon 6. The primers used to amplify this region of the ank gene were SEQ ID NOS: 92 and 93.
Local sequence context to confirm location:
gtctacagacNcttttcctta (SEQ ID NOS:113 and 114)

The instant invention is shown and described herein in what is considered to be the most practical, and preferred embodiments. It is recognized, however, that departures may be made therefrom, which are within the spirit and scope of the invention, and that obvious modifications will occur to one skilled in the art upon reading this disclosure. The scope of the invention is thus limited solely by the appended claims.

What is claimed is:

1. An isolated human progressive ankylosis (ANK) protein, wherein said human ANK protein comprises the amino acid sequence set forth in SEQ ID NO:2.

2. A method for identifying an agent that increases human ANK activity, the method comprising:

combining a candidate agent with a cell expressing human ANK protein wherein said human ANK protein comprises the amino acid sequence set forth in SEQ ID NO:2; and determining the effect of said agent on the levels of at least one of extracellular or intracellular pyrophosphate;

wherein with an increase in extracellular pyrophosphate and/or a decrease in intracellular pyrophosphate, the agent is indicative of increasing human activity.

3. The isolated human ANK protein according to claim 1 which is encoded by SEQ ID NO:1, residues 71–1549.

4. The method according to claim 2, wherein the effect of said agent on both intracellular and extracellular pyrophosphate is determined.

5. A method for identifying an agent that decreases human ANK activity, the method comprising:

combining a candidate agent with a cell expressing human ANK protein wherein said human ANK protein comprises the amino add sequence set forth in SEQ ID NO:2; and determining the effect of said agent on the levels of at least one of extracellular or intracellular pyrophosphate;

wherein with a decrease In extracellular pyrophosphate and/or an increase in intracellular pyrophosphate, the agent is indicative of decreasing human ANK activity.

6. The method according to claim 5, wherein the effect of said agent on both intracellular and extracellular pyrophosphate is determined.

* * * * *